(12) United States Patent
Hu et al.

(10) Patent No.: US 7,101,541 B2
(45) Date of Patent: Sep. 5, 2006

(54) UTILIZATION OF NON-VIRAL SEQUENCES FOR MINUS-STRAND DNA TRANSFER AND GENE RECONSTITUTION

(75) Inventors: Wei-Shau Hu, Frederick, MD (US); Vinay K. Pathak, Frederick, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 135 days.

(21) Appl. No.: 10/276,602

(22) PCT Filed: May 15, 2001

(86) PCT No.: PCT/US01/15739

§ 371 (c)(1),
(2), (4) Date: May 21, 2003

(87) PCT Pub. No.: WO01/90391

PCT Pub. Date: Nov. 29, 2001

(65) Prior Publication Data

US 2004/0048379 A1 Mar. 11, 2004

Related U.S. Application Data

(60) Provisional application No. 60/205,395, filed on May 19, 2000.

(51) Int. Cl.
| | |
|---|---|
| *A01K 48/00* | (2006.01) |
| *A01K 63/00* | (2006.01) |
| *C12N 15/00* | (2006.01) |
| *C12N 15/09* | (2006.01) |
| *C12N 15/63* | (2006.01) |

(52) U.S. Cl. .................. 424/93.2; 424/93.1; 435/320.1; 536/24.1; 536/24.2; 536/23.5

(58) Field of Classification Search .................. 514/44; 424/93.1, 93.2; 536/23.5, 24.1, 24.2; 435/320.1
See application file for complete search history.

(56) References Cited

U.S. PATENT DOCUMENTS

| | | | |
|---|---|---|---|
| 4,830,965 A | 5/1989 | Narang et al. | 435/473 |
| 5,658,775 A | 8/1997 | Gilboa | 435/69.1 |
| 5,714,353 A | 2/1998 | Pathak et al. | 435/91.42 |
| 5,741,486 A | 4/1998 | Pathak et al. | 424/93.21 |
| 5,858,744 A | 1/1999 | Baum et al. | 435/456 |
| 5,925,345 A | 7/1999 | Blaese et al. | 424/93.2 |
| 6,013,517 A | 1/2000 | Respess et al. | 435/325 |

FOREIGN PATENT DOCUMENTS

| | | |
|---|---|---|
| WO | WO 97/06271 | 2/1997 |
| WO | WO 98/17816 | 4/1998 |
| WO | WO 99/35280 | 7/1999 |

OTHER PUBLICATIONS

Vogt (1997) Retroviruses, Editors Coffin, et al., Cold Spring Harbor Laboratory Press, Cold Spring Harbor, N.Y., p. 38–40.*
Deonarain (1998) Exp. Opin. Ther. Pat., 8(1): 53–69.*
Gorecki (2001) Exp. Opin. Emerging Drugs, 6(2): 187–98.*
Verma, et al. (1997) Nature, 389: 239–42.*
Eck, et al. (1996) Goodman & Gilman's The Pharmacological Basis of Therapeutics, 9th Ed., McGraw–Hill, New York, NY., pp. 77–101.*
Rabson, et al. (1997) Retroviruses, Editors: Coffin, et al., Cold Spring Harbor Laboratory Press, Plainview, NY, pp. 207–208, 212, 233.*
Walther, et al. (2000) Drugs, 60(2): 249–71.*
Talbotta, et al. (2001) J. Gene Med., 3: 418–26.*
Cheslock, et al. (2000) J. Virol., 74(20): 9571–79.*
Allain, et al. (1998) J. Mol. Biol. 277(2): 225–235.*
Adam et al., *Human Gene Therapy* 6:1169–1176 (1995).
Atlung et al., *Gene* 107:11–17 (1991).
Chen et al., *Biochemical and Biophysical Research Communication* 184(1):330–337 (1992).
Choulika et al., *Journal of Virology* 70(3) 1792–1798 (1996) (Abstract only).
Christ et al., *J. Mol. Biol.* 288:825–836 (1999).
Delviks et al., *Journal of Virology* 71(8):6218–6224 (1997).
Delviks et al., *Journal of Virology* 73(10):8837–8842 (1999).
Joshi et al., *Nucleic Acids Res.* 18(14):4223–4226 (1990) (Abstract only).
Julias et al., *Journal of Virology* 69(11):6839–6846 (1995).
Kaneko et al., *Gene* 215:57–67 (1998).
Lorbach et al., *J. Mol. Biol.* 296:1175–1181 (2000).
Olson et al., *Journal of Virology* 66(3):1336–1343 (1992).
Rasmussen et al., *Journal of Virology* 74(20):9571–9579 (2000).
Russ et al., *Journal of Virology* 70(8):4927–4932 (1996) (Abstract only).

\* cited by examiner

*Primary Examiner*—Joseph Woitach
*Assistant Examiner*—Robert M. Kelly
(74) *Attorney, Agent, or Firm*—Klarquist Sparkman LLP

(57) ABSTRACT

A retroviral vector for gene reconstitution is provided that includes a 3' portion of a heterologous nucleic acid sequence 5' of a first att site and a 5' portion of the heterologous nucleic acid sequence 3' of a second att site. A sub-portion of the 3' portion of the heterologous nucleic acid sequence and a sub-portion the 5' portion of the heterologous nucleic acid sequence are direct repeats. A retroviral vector for gene reconstitution is also provided that includes a 3' portion of a heterologous nucleic acid sequence inserted into or adjacent to a 5' retroviral terminal repeat of the retroviral vector, and a 5' portion of the heterologous nucleic acid sequence inserted into or adjacent to a 3' retroviral terminal repeat of the retroviral vector, wherein the 3' and the 5' retroviral terminal repeats each comprise an att site. Methods and kits are also provided.

49 Claims, 10 Drawing Sheets

Additional examples

A. Deletion of viral sequences

B. Deletion of non-viral sequences

UTILIZATION OF NON-VIRAL SEQUENCES FOR MINUS-STRAND DNA TRANSFER AND GENE RECONSTITUTION

PRIORITY CLAIM

This is a § 371 U.S. national stage of International Application No. PCT/US01/15739, filed May 15, 2001, which was published in English under PCT Article 21(2), and claims the benefit of U.S. Provisional Application No. 60/205,395 filed May 19, 2000.

FIELD OF THE INVENTION

This application relates to gene transfer using viral vectors, and specifically to the use of retroviral vectors for the transformation of eukaryotic cells.

BACKGROUND OF THE INVENTION

The transfer of genes into cells provides a means to determine gene function and treat diseases having a genetic basis. In addition, gene transfer provides the basis for high-level protein expression, used by molecular researchers to study protein function and to produce new protein drugs. The introduction of genes into animals can also produce useful animal models of human diseases.

Many methods have been developed to introduce exogenous genes into cells. The earliest method for introducing DNA into cells was to incubate the DNA with an inert carbohydrate polymer (dextran) to which a positively charged chemical group (DEAE) had been coupled. These large DNA-containing particles stuck to cells and were taken up by endocytosis. However, this method was inefficient for the introduction of nucleic acid into many types of cells. Another widely used method is the precipitation of DNA with calcium phosphate, which allows transient expression of genes in cells. However, neither of these methods allow the transfer of nucleic acids into a cell with a high efficiency, nor do they allow for persistent gene expression. Thus, a need remains for a high efficiency method for the stable introduction of genes into cells.

Viral vectors, such as adenoviral or retroviral vectors, have been used to introduce foreign DNA with high efficiency. Retroviruses are RNA viruses that replicate through a double-stranded DNA intermediate. After a retrovirus infects a host cell, the retroviral genomic RNA is reverse transcribed to the double stranded DNA form. This DNA can integrate into the host genome to form a provirus. Reverse transcription requires cis-acting viral sequences including the primer binding site (pbs), the repeat (R) region of the long terminal repeats (LTRs), and the polypurine tract (ppt). Viral terminal attachment sites (att) mediate the integration of the provirus into the host genome. The integrated provirus is transcribed into full-length and spliced mRNA These RNAs are used as templates to translate viral proteins. Full length mRNA is packaged by the viral proteins, which recognize viral RNA by the cis-acting E or ψ sequence. The viral particles, or virions, exit the cell by budding from the cell membrane.

Retroviral vectors containing parts of the retrovirus are used to introduce foreign DNA into eukaryotic cells. Retroviral vectors usually contain the cis-acting sequences required for packaging, reverse transcription, and integration. However, these vectors are replication incompetent because they are defective in retroviral structural genes. Helper cells containing helper virus DNA supply the deficient viral gene products. Thus by transfecting the replication incompetent retrovirus into helper cells, retroviral RNA can be packaged and released as vector virus particles. Because the helper virus is deficient in cis-acting functions, its RNA is not packaged, and helper-free viral stocks can be produced. The released vector-containing particles can be used to introduce the foreign DNA into target cells.

SUMMARY OF THE INVENTION

Novel retroviral vectors are disclosed herein for the introduction of heterologous nucleic acid into a host cell. Integration of these vectors into the nucleic acid of a host cell results in reconstitution and duplication of the heterologous nucleic acid in the cellular genome.

A retroviral vector for gene reconstitution is provided that includes a 3' portion of a heterologous nucleic acid sequence 5' of a first att site of the retroviral vector, a 5' portion of the heterologous nucleic acid sequence 3' of a second att site of the retroviral vector. In this vector, a sub-portion of the 3' portion of the heterologous nucleic acid sequence and the 5' region of the heterologous nucleic acid sequence are direct repeats. Transformation of a eukaryotic cell with the retroviral vector results in reconstitution and duplication of the heterologous nucleic acid sequence.

A retroviral vector for gene reconstitution is also provided that includes a 3' portion of a heterologous nucleic acid sequence inserted into or adjacent to a 5' retroviral terminal repeat of the retroviral vector, and a 5' portion of the heterologous nucleic acid sequence inserted into or adjacent to a 3' retroviral terminal repeat of the retroviral vector, wherein the 5' retroviral terminal repeat and the 3' retroviral terminal repeat each comprise an att site. A sub-portion of the 3' portion of the heterologous nucleic acid sequence and the 5' region of the heterologous nucleic acid sequence are direct repeats. Transformation of a eukaryotic cell with this retroviral vector results in reconstitution and duplication of the heterologous nucleic acid sequence.

In one embodiment, a method is provided for reconstituting and duplicating a nucleic acid molecule in a host cell is by transforming the host cell with a retroviral vector. The vector includes a 3' portion of a heterologous nucleic acid sequence inserted into or adjacent to a 5' retroviral terminal repeat of the retroviral vector, and a 5' portion of the heterologous nucleic acid sequence inserted into or adjacent to a 3' retroviral terminal repeat of the retroviral vector, wherein a sub-portion of the 3' portion of the heterologous nucleic acid sequence and the 5' region of the heterologous nucleic acid sequence are direct repeats. The transformation of the host cell results in viral integration and production of a 5' long terminal repeat and a 3' long terminal repeat, thereby reconstituting and duplicating the nucleic acid sequence within the 5' and the 3' long terminal repeats.

In another embodiment, a method is provided for transforming a cell. The method includes contacting the cell with a retroviral vector comprising a 3' portion of a heterologous nucleic acid sequence inserted into or adjacent to a 5' retroviral terminal repeat of the retroviral vector, and a 5' portion of the heterologous nucleic acid sequence inserted into or adjacent to a 3' retroviral terminal repeat of the retroviral vector, wherein a sub-portion of the 3' portion of the heterologous nucleic acid sequence and the 5' region of the heterologous nucleic acid sequence are direct repeats. The contact results in transformation of the cell.

A kit is also provided that includes a packaging means for a retroviral vector for gene reconstitution. The vector includes a 3' portion of a nucleic acid sequence inserted into, or adjacent to, a 5' retroviral terminal repeat of the retroviral vector, and a 5' portion of the nucleic acid sequence inserted into, or adjacent to, a 3' retroviral terminal repeat of the retroviral vector, wherein a sub-portion of the 3' portion of the gene and the 5' region of the gene are direct repeats.

In a further embodiment, a method is provided for treating a subject that includes contacting a cell of the subject with a therapeutically effective amount of a retroviral vector for gene reconstitution. The retroviral vector includes a 3' portion of a heterologous nucleic acid sequence 5' of a first att site of the retroviral vector and a 5' portion of the heterologous nucleic acid sequence 3' of a second att site of the retroviral vector. A sub-portion of the 3' portion of the heterologous nucleic acid sequence and the 5' region of the heterologous nucleic acid sequence are direct repeats. The contact of the cell with the retroviral vector results in integration of the retroviral vector in the cellular genome, and the subject is treated.

DETAILED DESCRIPTION OF THE SPECIFIC EMBODIMENTS

Figure 1:
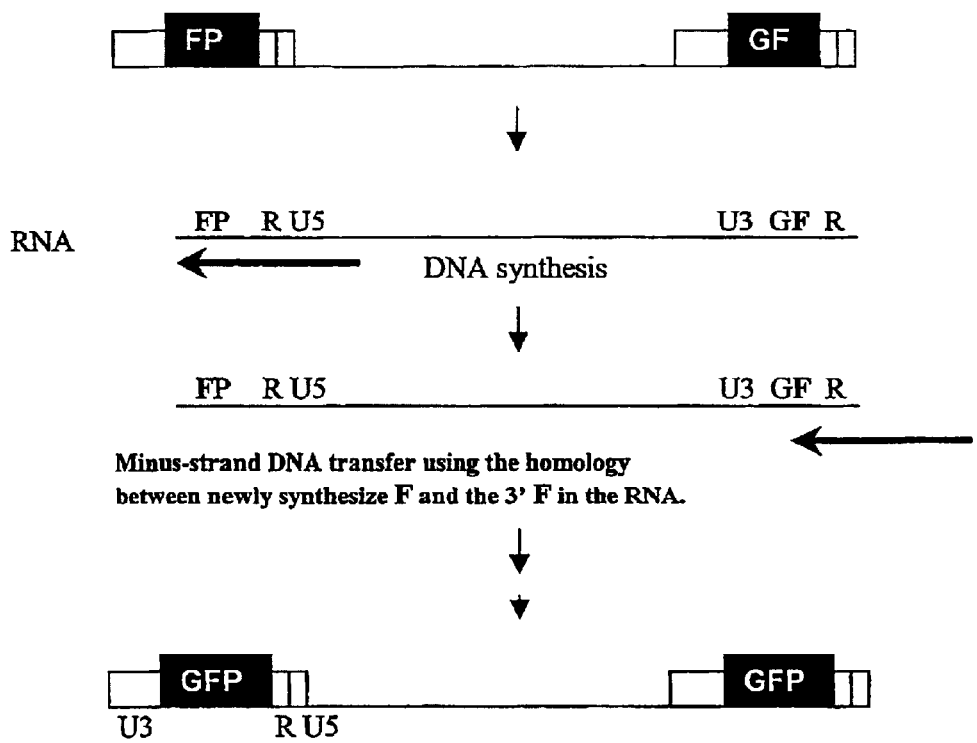
FIG. 1 is a diagram of the use of a retroviral vector including a 5' portion of a heterologous nucleic acid, and a 3' portion of a heterologous nucleic acid, to reconstitute and duplicate complete a heterologous nucleic acid in a cell transduced with the retrovirus.

The following definitions and methods are provided to better define the present invention, and to guide those of ordinary skill in the art in the practice of the present invention. It must be noted that as used herein and in the appended claims, the singular forms "a", "an", and "the" include plural referents unless the context clearly dictates otherwise. Thus, for example, reference to "a cell" includes a plurality of such cells and reference to "the vector" includes reference to one or more vectors and equivalents thereof known to those skilled in the art, and so forth.

Unless defined otherwise, all technical and scientific terms used herein have the same meaning as commonly understood to one of ordinary skill in the art to which this invention belongs.

DEFINITIONS

Animal: Living multicellular vertebrate organisms, a category which includes, for example, mammals and birds.

Antisense, Sense, and Antigene: Double-stranded DNA (dsDNA) has two strands, a 5'→3' strand, referred to as the plus strand, and a 3'→5' strand, referred to as the minus strand. Because RNA polymerase adds nucleic acids in a 5'→3' direction, the minus strand of the DNA serves as the template for the RNA during transcription. Thus, the RNA formed will have a sequence complementary to the minus strand, and identical to the plus strand (except that the base uracil is substituted for thymine).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target.

Attachment site (att): A cis acting nucleic acid element, recognized by integrase, which facilitates efficient integration of a virus into host genome. In one specific non-limiting example, an attachment site is from about 7 to about 13 nucleotides in length (see Murphy et al. Virology 195: 432–440, 1993). In another specific, non-limiting example, an att site is from about 5 to about 15 nucleotides in length. In one specific non-limiting example, the att site is from 10 to 15 base pairs in length and includes the terminal 4 base pairs found in the native retroviral att site (e.g. the terminal 4 base pairs of a MLV, a SNV, or a lentiviral att site). In the RNA form of a retrovirus, there are two att sites: one att site at the 3' end of the U5 element, and an additional att site at the 5' end of the U3 element. In the DNA form of a retrovirus, there are two sets of att sites (in a naturally-occurring retrovirus), one set at the 5' end of U3 elements and one set at the 3' end of U5 elements.

In one embodiment, a retroviral vector can include an att site adjacent to a heterologous nucleic acid sequence or a portion thereof, so that the 3' end of the att site is from about 0 (e.g. directly adjacent to the heterologous sequence) to about 20 nucleotides away from the 5' end of the heterologous nucleic acid or portion thereof. In another embodiment, a retroviral vector can include an att site 5' or 3' of a portion of the heterologous nucleic acid sequence, so that the att site is located from about 0 (e.g. adjacent to the heterologous nucleic acid) to about 1000 bases away from the terminus of the heterologous nucleic acid sequence. In yet another embodiment, the att site is located up to about 3000 bases away form the terminus of the heterolgous nucleic acid sequence.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional or physical binding assays. Binding may be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, a method which is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target dissociate or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Capsid: The protein covering, or outer coat, of a virus particle. The capsid is a protein coat that covers the nucleoprotein core or nucleic acid of a virion. The capsid generally shows icosahedral symmetry and in some viruses is enclosed in an envelope. The capsid is built up of subunits (some integer multiple of 60, the number required to give strict icosahedral symmetry) that self assemble in a pattern typical of a particular virus. The subunits are often packed, in smaller capsids, into 5 or 6 membered rings (pentamers or hexamers) that constitute the morphological unit (capsomere). A capsid is required for viral infection of a cell.

Direct Repeat: A nucleotide sequence that is repeated, so that when read in the 5' to 3' direction (see below), the sequence and its repeat are substantially identical. In one embodiment, the repeats have 100% sequence identity. In another embodiment the repeats have 95% sequence identity. In yet another embodiment, the repeats are 90% identical or 85% identical.

Duplication: The process of replicating a copy of a nucleic acid sequence, so that the nucleic acid sequence is reproduced. In one embodiment, the replicated copy of the nucleic acid sequence is in a different location than the original copy of the nucleic acid sequence.

Envelope polypeptide or Env: An "env" polypeptide is a retroviral "envelope" protein which encodes the surface (SU) glycoprotein and the transmembrane (TM) protein of the virion. The SU glycoprotein and the TM protein form a complex that interacts specifically with cellular receptors.

Essential Gene: A gene required for viral replication, packaging or infection. Deletion of an essential gene renders a virus replication defective. For example, in a retroviral, gag, pol and env (see below) are essential genes.

Functional Deletion: A mutation in a sequence that has an effect equivalent to deletion of the sequence, for example eliminating the function of a packaging signal or an essential gene product by a deletion, insertion, or substitution.

Functionally Equivalent: Sequence alterations, in either the transfer or packaging vector sequences, that yield the same results as described herein. Such sequence alterations can include, but are not limited to, conservative substitutions, deletions, mutations, frameshifts, and insertions.

Gene, Genome, and Genetic Target: The terms "gene," "genome," and "genetic target" include both DNA and RNA. Generally, a gene is a sequence of DNA or RNA that codes for a protein. A "target" sequence is a sequence to which an antisense or sense oligonucleotide or analog specifically hybridizes.

Group Specific Antigen Polypeptide or Gag: A "gag" protein is a retroviral "group specific antigen" polypeptide which is proteolytically processed into the mature proteins MA (matrix), CA (capsid), and NC (nucleocapsid), and other proteins that are numerically designated.

Heterologous: A heterologous sequence is a nucleic acid sequence that is not normally (i.e. in the wild-type sequence) found adjacent to a second nucleic acid sequence. In one embodiment, the heterologous (first) nucleic acid sequence is from a different genetic source, such as a virus or organism, than the second nucleic acid sequence. A heterologous nucleic acid sequence can be of any length. In one embodiment, a heterologous nucleic acid sequence encodes a polypeptide. In another embodiment, a heterologous nucleic acid sequence encodes an antisense oligonucleotide or a ribozyme that hybridizes to a genetic target sequence.

Integration: A virus "integrates" into cellular DNA when the nucleic acid of the virus is incorporated into the cellular genome (i.e. into a chromosome).

Infective: A virus or vector is "infective" when it transduces a cell, replicates, and (without the benefit of any complementary virus or vector) spreads progeny vectors or viruses of the same type as the original transducing virus or vector to other cells in an organism or cell culture, where the progeny vectors or viruses have the same ability to reproduce and spread throughout the organism or cell culture. Thus, for example, a nucleic acid encoding a retroviral particle is not infective if the nucleic acid cannot be packaged (e.g. if the retroviral particle lacks a packaging site), even though the nucleic acid can be used to transfect a cell. Similarly, a retroviral nucleic acid packaged by an retroviral particle is not infective if it does not encode the retroviral capsid proteins that it is packaged in.

Integration: The insertion of retroviral nucleic acid into the host cell's nucleic acid, following transformation of a host cell. Integration is catalyzed by the integrase polypeptide, which is part of the reverse transcriptase complex. Integration is a highly specific reaction with respect to the retroviral provirus, but the region of the host cell DNA where the retrovirus integrates is random.

Isolated: An "isolated" nucleic acid has been substantially separated or purified away from other nucleic acid sequences and in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

Mammal: This term includes both human and non-human mammals. Similarly, the term "subject" includes both human and veterinary subjects.

Nucleic acid sequence (or polynucleotide): A deoxyribonucleotide or ribonucleotide polymer in either single or double stranded form, and unless otherwise limited, encompasses known analogues of natural nucleotides that hybridize to nucleic acids in a manner similar to naturally occurring nucleotides, and includes polynucleotides encoding full length proteins and/or fragments of such full length proteins which can function as a therapeutic agent.

A nucleic acid sequence consists of nucleotides linked together by covalent phosphodiester bonds that join the 5' carbon of one deoxyribose or ribose group to the 3' carbon of the next. Thus, a linear nucleic acid sequence has a 5' end and a 3' end. A 5' portion of a nucleic acid sequence is located 5' of a given reference sequence. In one embodiment, the 5' portion of a nucleic acid sequence includes the terminal 5' nucleotide of the nucleic acid. A 3' portion of a nucleic acid sequence is located 3' of a given reference sequence. In one embodiment, the 3' portion of a nucleic acid sequence includes the terminal 3' nucleotide of the nucleic acid sequence. The portions of the nucleic acid sequence can be of any length. In one embodiment, they are less than about 1 kb in length. In another embodiment they are less than 7 kb in length.

A "sub-portion" of a nucleic acid sequence is a defined nucleic acid sequence that is included in a portion of the nucleic acid sequence. In one embodiment, a sub-portion of a nucleic acid sequence is at least 6 nucleotides in length. In another embodiment, the sub-portion of a nucleic acid sequence is from about 12 to about 1500, or about 1000 nucleotides in length.

A polynucleotide is generally a linear nucleotide sequence, including sequences of at least 20 nucleotide bases in length. A first polynucleotide sequence is adjacent to a second polynucleotide sequence if the 5' or 3' end of the first polynucleotide sequence is within zero to about ten nucleotides of the 3' or 5' end, respectively, of the second polynucleotide sequence Nucleotide: "Nucleotide" includes, but is not limited to, a monomer that includes a base linked to a sugar, as in DNA and RNA, or a base linked to an amino acid, as in a peptide nucleic acid (PNA). A nucleotide is one monomer in a polynucleotide. A nucleotide sequence refers to the sequence of bases in a polynucleotide.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Packaging cell: A cell that provides packaging functions in trans for a gene introduced into a cell with a transfer vector, but which does not encapsidate its own viral RNA.

Packaging Signal: A complex signal, also known as "ψ", or "E" (e.g., for SNV) that is important for the packaging of virus in viral particles.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Additional definitions of common terms in molecular biology may be found in Lewin, B., "Genes V" published by Oxford University Press.

Polymerase or Pol: A "pol" protein is a retroviral reverse transcriptase, which contains both DNA polymerase and associated RNAse H activities, and Integrase (IN). Pol mediates replication of the viral genome in vivo. The ends of the newly synthesized linear double-stranded viral DNA are recognized and two nucleotides from the 3' end of each strand are removed. These DNA ends are joined to a target DNA at random sites.

Polypeptide: Any chain of amino acids, regardless of length or post-translational modification (e.g., glycosylation or phosphorylation). In one embodiment, a polypeptide can be a "marker" polypeptide, which is used to identify cells that express the polypeptide. A marker polypeptide can be detected using methods known to one of skill in the art, including enzymatic assays, spectrophotometric assays, and assays utilizing antibodies (e.g. ELISA or immunohistochemistry). Specific non-limiting examples of a maker protein are luciferase, green fluorescent protein (GFP), or beta-galactosidase. Other specific, non-limiting examples of proteins of use are proteins that make a cell drug resistance (e.g. zeomycin bleomycin resistant), such as a neomycin transferase, a hygromycin phosphotransferase, or a puromycin resistance polypeptide. In another embodiment, a polypeptide is a "therapeutic" polypeptide, which can be used to alleviate or relieve a symptom of a disorder. Specific, non-limiting examples of therapeutic polypeptides are cytokines or immunomodulators, hormones, neurotransmitters, antigens, or enzymes. Specific non-limiting examples of cytokines are IL-2, IL-4, IL-6, IL-8, IL-12, TNF-α, TNF-β, and IFN-γ. In another embodiment, a polypeptide is an enzyme. Specific, non-limiting examples of enzymes are horse radish peroxidase and alkaline phosphatase.

Probes and primers: A probe comprises an isolated nucleic acid attached to a detectable label or reporter molecule. Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art. One of skill in the art will appreciate that the specificity of a particular probe or primer increases with its length. Thus, for example, a primer comprising 20 consecutive contiguous nucleotides from a DNA sequence will anneal to a target with a higher specificity than a corresponding primer of only 15 contiguous nucleotides. Thus, in order to obtain greater specificity, probes and primers may be selected that comprise 20, 25, 30, 35, 40, 50 or more contiguous nucleotides.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements.

Provirus: A retroviral provirus is a double-stranded DNA product formed by reverse transcription of a retroviral RNA. The proviral DNA is longer than the viral RNA by one U3, R, U5 sequence. As a result, there is a direct repeat of the U3, R, U5 sequence, known a long terminal repeat (LTR), present at each end of the provirus genome (see above).

Purified: The term purified does not require absolute purity; rather, it is intended as a relative term. Thus, for example, a purified protein preparation is one in which the protein is more pure than the protein in its natural environment within a cell. For example, a preparation of a protein is purified such that the protein represents at least 50% of the total protein content of the preparation.

R Region: A short (12–250 nt) sequence which forms a direct repeat at the both ends of the retroviral genome, which is therefore terminally redundant.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Reconstitution: To restore a nucleic acid sequence to its original form. Thus, if a nucleic acid sequence is divided into a 5' portion and a 3' portion, reconstitution of the nucleic acid sequence results in the 5' portion and the 3' portion being joined to form the original nucleic acid sequence.

Replication defective: A virus is replication defective if it cannot replicate in a host cell.

Retrovirus: Any virus in the family Retroviridae. These viruses have similar characteristics, specifically they share a replicative strategy. This strategy includes as essential steps reverse transcription of the virion RNA into linear double-stranded DNA, and the subsequent integration of this DNA into the genome of the cell. All native retroviruses contain three major coding domains with information for virion proteins: gag, pol and env. In one embodiment, a retrovirus is an avian sarcoma and leukosis virus, a mammalian B-type virus, a Murine leukemia-related virus, a Human T-cell leukemia-bovine leukemia virus, a D-type virus, a lentivirus, or a spumavirus. In another embodiment, the virus is a Rous sarcoma virus, a mouse mammary tumor virus, a human T-cell leukemia virus, a Mason-Pzifer monkey virus, a human immunodeficiency virus, a human foamy virus, or a Molony Leukemia Virus. A retrovirus generally contains three genes known as "gag," "pol," and "env."

RNA: All types of RNA, including viral genomic RNA and mRNA.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of nucleic acid or amino acid sequences will possess a relatively high degree of sequence identity when aligned using standard methods. This homology will be more significant when the orthologous proteins or nucleic acids are derived from species which are more closely related (e.g., human and chimpanzee sequences), compared to species more distantly related (e.g., human and C. elegans sequences). Typically, orthologs are at least 50% identical at the nucleotide level and at least 50% identical at the amino acid level when comparing human orthologous sequences.

Methods of alignment of sequences for comparison are well known. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237–44, 1988; Higgins & Sharp, CABIOS 5:151–3, 1989; Corpet et al., Nuc. Acids Res. 16:10881–90, 1988; Huang et al. Computer Appls. Biosci. 8, 155–65, 1992; and Pearson et al., Meth. Mol. Bio. 24:307–31, 1994. Altschul et al., J. Mol. Biol. 215:403–10, 1990, presents a detailed consideration of sequence alignment methods and homology calculations.

The NCBI Basic Local Alignment Search Tool (BLAST) (Altschul et al., J. Mol. Biol. 215:403–10, 1990) is available from several sources, including the National Center for Biotechnology Information (NCBI, Bethesda, Md.) and on the Internet, for use in connection with the sequence analysis programs blastp, blastn, blastx, tblastn and tblastx. Each of these sources also provides a description of how to determine sequence identity using this program.

Homologous sequences are typically characterized by possession of at least 60%, 70%, 75%, 80%, 90%, 95% or at least 98% sequence identity counted over the full length alignment with a sequence using the NCBI Blast 2.0, gapped blastp set to default parameters. Queries searched with the blastn program are filtered with DUST (Hancock and Armstrong, Comput. Appl. Biosci. 10:67–70, 1994). It will be appreciated that these sequence identity ranges are provided for guidance only; it is entirely possible that strongly significant homologs could be obtained that fall outside of the ranges provided.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that all encode substantially the same protein.

One indication that two nucleic acid sequences are substantially identical is that the polypeptide encoded by the first nucleic acid is immunologically cross reactive with the polypeptide encoded by the second nucleic acid.

An alternative indication that two nucleic acid molecules are closely related is that the two molecules hybridize to each other under stringent conditions, as described under "specific hybridization."

Specific hybridization: Specific hybridization refers to the binding, duplexing, or hybridizing of a molecule only or substantially only to a particular nucleotide sequence when that sequence is present in a complex mixture (e.g. total cellular DNA or RNA). Specific hybridization may also occur under conditions of varying stringency.

Hybridization conditions resulting in particular degrees of stringency will vary depending upon the nature of the hybridization method of choice and the composition and length of the hybridizing DNA used. Generally, the temperature of hybridization and the ionic strength (especially the Na+ concentration) of the hybridization buffer will determine the stringency of hybridization. Calculations regarding hybridization conditions required for attaining particular degrees of stringency are discussed by Sambrook et al. (In: *Molecular Cloning: A Laboratory Manual*, Cold Spring Harbor, N.Y., 1989, chapter 9 and 11). By way of illustration only, a hybridization experiment may be performed by hybridization of a DNA molecule to a target DNA molecule which has been electrophoresed in an agarose gel and transferred to a nitrocellulose membrane by Southern blotting (Southern, *J. Mol. Biol.* 98:503, 1975), a technique well known in the art and described in Sambrook et al. (*Molecular Cloning: A Laboratory Manual*, Cold Spring Harbor, N.Y., 1989).

Hybridization with a target probe labeled with [$^{32}$P]-dCTP is generally carried out in a solution of high ionic strength such as 6×SSC at a temperature that is 20–25° C. below the melting temperature, $T_m$, described below. For Southern hybridization experiments where the target DNA molecule on the Southern blot contains 10 ng of DNA or more, hybridization is typically carried out for 6–8 hours using 1–2 ng/ml radiolabeled probe (of specific activity equal to $10^9$ CPM/µg or greater). Following hybridization, the nitrocellulose filter is washed to remove background hybridization. The washing conditions should be as stringent as possible to remove background hybridization but to retain a specific hybridization signal.

The term $T_m$ represents the temperature (under defined ionic strength, pH and nucleic acid concentration) at which 50% of the probes complementary to the target sequence hybridize to the target sequence at equilibrium. Because the target sequences are generally present in excess, at Tm 50% of the probes are occupied at equilibrium. The $T_m$ of such a hybrid molecule may be estimated from the following equation (Bolton and McCarthy, *Proc. Natl. Acad. Sci. USA* 48:1390, 1962):

$$T_m = 81.5° C. - 16.6(\log_{10}[Na^+]) + 0.41(\% G+C) - 0.63(\% \text{formamide}) - (600/1)$$

where 1=the length of the hybrid in base pairs.

This equation is valid for concentrations of Na$^+$ in the range of 0.01 M to 0.4 M, and it is less accurate for calculations of Tm in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al. (*Molecular Cloning: A Laboratory Manual*, Cold Spring Harbor, N.Y., 1989).

Thus, by way of example, for a 150 base pair DNA probe derived from a cDNA (with a hypothetical % GC of 45%), a calculation of hybridization conditions required to give particular stringencies may be made as follows: For this example, it is assumed that the filter will be washed in 0.3×SSC solution following hybridization, thereby: [Na+]= 0.045 M; % GC=45%; Formamide concentration=0; 1=150 base pairs; Tm=81.5−16.6(log$_{10}$[Na+])+(0.41×45)−(600/150); and so Tm=74.4° C.

The $T_m$ of double-stranded DNA decreases by 1–1.5° C. with every 1% decrease in homology (Bonner et al., *J. Mol. Biol.* 81:123, 1973). Therefore, for this given example, washing the filter in 0.3×SSC at 59.4–64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4–68.4° C. will yield a hybridization stringency of 94%; that is, DNA molecules with more than 6% sequence variation relative to the target cDNA molecule will not hybridize. The above example is given entirely by way of theoretical illustration. It will be appreciated that other hybridization techniques may be utilized and that variations in experimental conditions will necessitate alternative calculations for stringency.

In the present invention, stringent conditions may be defined as those under which DNA molecules with more than 25%, 15%, 10%, 6% or 2% sequence variation (also termed "mismatch") will not hybridize. Stringent conditions are sequence dependent and are different in different circumstances. Longer sequences hybridize specifically at higher temperatures. Generally, stringent conditions are selected to be about 5° C. lower than the thermal melting point $T_m$ for the specific sequence at a defined ionic strength and pH. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na Phosphate, 5 mM EDTA, pH 7.4) and a temperature of 25–30° C. are suitable for allele-specific probe hybridizations.

A perfectly matched probe has a sequence perfectly complementary to a particular target sequence. The test probe is typically perfectly complementary to a portion (subsequence) of the target sequence. The term "mismatch probe" refers to probes whose sequence is deliberately selected not to be perfectly complementary to a particular target sequence.

Transcription levels can be quantitated absolutely or relatively. Absolute quantitation can be accomplished by inclusion of known concentrations of one or more target nucleic acids (for example control nucleic acids or with a known amount the target nucleic acids themselves) and referencing the hybridization intensity of unknowns with the known target nucleic acids (for example by generation of a standard curve).

Supernatant: The culture medium in which a cell is grown. The culture medium includes material from the cell. If the cell is infected with a virus, the supernatant can include viral particles.

Target sequence: "Target sequence" is a portion of ssDNA, dsDNA or RNA that, upon hybridization to a therapeutically effective antisense oligonucleotide or oligonucleotide analog, results in the inhibition of expression of the target sequence. Either an antisense or a sense molecule can be used to target a portion of dsDNA, since both will interfere with the expression of that portion of the dsDNA. The antisense molecule can bind to the plus strand, and the sense molecule can bind to the minus strand. Thus, target sequences can be ssDNA, dsDNA, and RNA.

Terminal Repeat: A terminal repeat is a nucleic acid sequence repeated at both ends of a retrovirus. An "LTR" is a "long terminal repeat" that is generated as a DNA duplex at both ends of the retrovirus when a retrovirus integrates into a host genome. The 5' LTR includes a U3, R, and U5 nucleic acid element. The 3' LTR also includes U3, R, and U5 nucleic acid element. In a replication competent retrovirus, LTRs also contain an active RNA polymerase II promoter which allows transcription of the integrated provirus by host cell RNA polymerase II to generate new copies of the retroviral RNA genome.

An integrated retrovirus has two LTRs, one at the 5' end and one at the 3' end of the viral genome. The "5' LTR" is located at the 5' end of the retroviral DNA, and the "3' LTR" is located at the 3' end of the retroviral DNA.

A heterologous nucleic acid sequence or a portion thereof can be inserted into a terminal repeat or an element thereof, such as into an LTR, so that a portion of the terminal repeat is on the 5' end and the 3' end of the heterologous nucleic acid sequence. Alternatively, a heterologous nucleic acid sequence or a portion thereof can be adjacent to a terminal repeat or an element thereof, so that the terminal repeat or element thereof is located on either 3' or 5' or the heterologous nucleic acid sequence or portion thereof.

Therapeutically effective amount: An amount of a therapeutic protein or antisense molecule effective to inhibit or treat a disease or its symptoms. Although this amount varies depending on the severity and nature of a condition being treated, examples of effective amounts are tissue concentrations that are effective to provide relief of a symptom.

Therapeutically Effective Oligonucleotides: Characterized by their ability to inhibit the expression of a gene of interest. Complete inhibition is not necessary for therapeutic effectiveness. Therapeutically effective oligonucleotides are characterized by their ability to inhibit the expression of the gene of interest. Inhibition is defined as any reduction in expression seen when compared to production in the absence of the oligonucleotide or oligonucleotide analog. Additionally, some oligonucleotides will be capable of inhibiting the expression of a gene of interest by at least 15%, 30%, 40%, 50%, 60%, or 70%, or more.

Therapeutically effective oligonucleotides are additionally characterized by being sufficiently complementary to nucleic acid sequences encoding a gene of interest. As described herein, sufficiently complementary means that the therapeutically effective oligonucleotide can specifically disrupt the expression of a gene, and not significantly alter the expression of other genes.

Transduced and Transformed: A virus or vector "transduces" a cell when it transfers nucleic acid into the cell. A cell is "tansformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgene: A nucleic acid sequence, such as a heterologous nucleic acid sequence supplied by a vector. In one embodiment the nucleic acid sequence encodes a marker protein which can be detected using methods known to one of skill in the art. Specific non-limiting examples of a marker protein are luciferase, green fluorescent protein (GFP), or beta-galactosidase. In another embodiment, the nucleic acid sequence encodes a protein, such as a therapeutic protein, which can be used to alleviate or relieve a symptom of a disorder. Specific, non-limiting examples of therapeutic proteins are cytokines or immunomodulators, hormones, neurotransmitters, or enzymes. In another embodiment, the nucleic acid sequence encodes a therapeutically effective oligonucleotide (e.g. an antisense oligonucleotide), wherein expression of the oligonucleotide inhibits the expression of a target nucleic acid sequence. In a further embodiment, the nucleic acid sequence encodes an antisense nucleic acid or a ribozyme.

The nucleic acid sequence can have the native regulatory sequences operably linked to the nucleic acid sequence (e.g. the wild-type promoter, found operably linked to the gene in a wild-type cell). Alternatively, a heterologous promoter can be operably linked to the nucleic acid sequence. In yet another embodiment, a retroviral promoter can be used to express the transgene.

U3: A unique non-coding region of 200–1,200 nucleotides, which forms the 5' end of a retroviral provirus after reverse transcription. In one embodiment, the U3 region contains the promoter elements responsible for transcription of the retroviral provirus. In another embodiment, the U3 promoter element is replaced with a heterologous promoter.

U3 includes an attachment site (att, see above). The att is at the 5' of the U3 region, and is essential for efficient viral integration. At a minimum, the U3 region of the 3' terminal repeat includes the att sequence.

U5: A unique, non-coding region of 75–250 nucleotides of the retroviral genome. The U5 region is the first part of the retroviral genome to be reverse transcribed, forming the 3' end of the provirus genome. U5 often plays an important role for the initiation of reverse transcription. U5 also includes an attachment (att) site (see above).

Variant oligonucleotides and variant analogs: A variation of an oligonucleotide or an oligonucleotide analog is an oligomer having one or more base substitutions (for example, 1, 2, 3, 5, or 10 substitutions), one or more base deletions (for example, 1, 2, 3, 5, or 10 deletions), and/or one or more base insertions (for example, 1, 2, 3, 5, or 10 insertions), so long as the oligomer substantially retains the activity of the original oligonucleotide or analog, or has sufficient complementarity to a target sequence.

A variant oligonucleotide or analog may also hybridize with the target DNA or RNA, under stringency conditions as described above. A variant oligonucleotide or analog also exhibits sufficient complementarity with the target DNA or RNA of the original oligonucleotide or analog as described above.

Vector: A nucleic acid molecule as introduced into a host cell, thereby producing a transformed host cell. A vector may include nucleic acid sequences that permit it to replicate in the host cell, such as an origin of replication. A vector may also include nucleic acid sequences encoding one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. A vector may be a viral vector, derived from a virus, such as a retroviral vector.

Viral Vectors and Viruses

Retroviruses are RNA viruses that replicate through a DNA intermediate. An essential step during the replication is copying the viral RNA into viral DNA (reverse transcription). Reverse transcription initiates near the 5' end of the viral RNA to synthesize a short piece of the minus-strand strong-stop DNA. This DNA is then transferred to the 3' end of the viral RNA using the complementarity between the R region in the newly synthesized DNA and the R region in the 3' end of the viral RNA. This step is referred to as the minus-strand DNA transfer. After minus-strand DNA transfer, reverse transcription continues to generate a double-stranded DNA copy of the viral genome.

Without being bound by theory, the retroviral vectors described herein use the process of minus-strand DNA transfer to reconstitute heterologous nucleic acid sequence. As minus-strand DNA transfer is an obligatory step of viral replication, a very high efficiency of reconstitution of a nucleic acid sequence is achieved.

In one embodiment, a retroviral vector for gene reconstitution is provided that includes a 3' portion of a heterologous nucleic acid sequence 5' of a first att site of the retroviral vector, and a 5' portion of the heterologous nucleic acid sequence 3' of a second att site of the retroviral vector. A sub-portion of the 3' portion of the heterologous nucleic acid sequence and the 5' portion of the heterologous nucleic acid sequence are direct repeats. Transformation of a eukaryotic cell with the retroviral vector results in reconstitution and duplication of the heterologous nucleic acid sequence. The first and the second att sites are from about 5 to about 15 nucleotides in length, and can be from about 7 to about 13 nucleotides in length.

The first att site can be included in the retroviral vector without the presence of additional retroviral terminal repeat sequences, or can be included as part of a 5' retroviral terminal repeat, such as a U5 sequence, or a fragment thereof. The second att site can also be included in the retroviral vector without the presence of additional retroviral terminal repeat sequences, or can be included in the vector along with part of a 3' retroviral terminal repeat, such as a U3 sequence, or a fragment thereof. The first att site can be adjacent to a portion of a heterologous nucleic acid sequence (see below), or the att site can be located from about 0 to about 1000 base pairs away from the portion of the heterologous nucleic acid sequence, or from about 1 to about 3000 base pairs from the portion of the heterologous nucleic acid sequence. Similarly, the second att site can be adjacent to a portion of a heterologous nucleic acid sequence (see below), or the att site can be located from about 0 to about 1000 base pairs away from the portion of the heterologous nucleic acid sequence, or from about 1 to about 3000 base pairs from the portion of the heterologous nucleic acid sequence. A sub-portion of the 5' portion of the heterologous nucleic acid and a sub-portion of the 3' portion of the heterologous nucleic acid are direct repeats. In one embodiment, the repeats are 100% identical. In other embodiments, the repeats are 95%, 90%, 85% or 80% identical.

In another embodiment, a retroviral vector for gene reconstitution includes a 3' portion of a heterologous nucleic acid sequence inserted into or adjacent to a 5' retroviral terminal repeat of the retroviral vector; and a 5' portion of the heterologous nucleic acid sequence inserted into or adjacent to a 3' retroviral terminal repeat of the retroviral vector. The 5' retroviral terminal repeat and the 3' retroviral terminal repeat each comprise an att site. In addition, a sub-portion of the 3' portion of the heterologous nucleic acid sequence and the 5' region of the heterologous nucleic acid sequence are direct repeats. Thus, transformation of a eukaryotic cell with the retroviral vector results in reconstitution and duplication of the heterologous nucleic acid sequence.

The process of reconstituting a nucleic acid sequence using a retroviral vector described herein is illustrated in one specific example diagramed in FIG. 1. In this approach a nucleic acid sequences is divided into two portions, a 5' portion, and a 3' portion. The 5' portion and the 3' have a sub-portion which is homologous. The homologous sub-portion is at least six nucleotides in length, and can be from about 12 to about 1500 nucleotides in length. In one embodiment, the subportion is 1000 nucleotides in length.

In the illustrated example, the heterologous nucleic acid encodes green fluorescent protein (GFP). The 5' portion is indicated as "GF" and the 3' portion is indicated as "FP." Thus, the homologous sub-portion is indicated as "F." The 3' portion is inserted into the 5' terminal repeat, such as a long terminal repeat (LTR) and the 5' half in the 3' terminal repeat, such as a long terminal repeat (LTR). The retroviral vector is then introduced into a host cell. After one round of retroviral replication in a host cell the heterologous gene is reconstituted, producing full length heterologous nucleic acid (e.g., GFP), and duplicated, so that two copies of the heterologous nucleic acid are integrated into the host genome.

The vectors and methods disclosed herein have numerous applications. Specific, non-limiting examples are the reconstitution of toxic genes for cancer therapy. Because the toxic gene is not in an active form during virus propagation, the growth of the virus is not impeded during production. However, when a cancer cell is infected, the toxic gene is reconstituted thereby killing the cancer cell.

In addition, the retroviral vectors described herein provide a sensitive assay for the detection of replication competent retrovirus during growing the virus for any application. Furthermore, the vectors and methods described herein can be used to regulate expression of a nucleic acid sequence, either in vivo or in vitro.

Heterologous Nucleic Acid Sequences for Transfer into a Cell

The heterologous nucleic acid sequence can be any sequence of interest. In one embodiment, the heterologous nucleic acid sequence is a nucleic acid sequence encoding a marker (e.g. luciferase (luc), β-galactosidase (β-gal), or green fluorescent protein (GFP)). In another embodiment, the heterologous sequence encodes a protein conferring antibiotic resistance, such as hygromycin, neomycin, or puromycin resistance.

In another embodiment, the heterologous nucleic acid sequence encodes a toxin. In this embodiment, the portions of the heterologous nucleic acid are not individually toxic when included in the virus. Rather, integration of the virus into the genome of a host cell results in reconstitution and duplication of the nucleic acid encoding the toxin, and thus the production of the toxic polypeptide product only once the virus is integrated into the cellular genome. Specific, non-limiting examples of toxins include diphtheria toxin, pseudomonas exotoxin, Herpesvirus thymidine knase, cytosine deaminase, and ricin In yet another embodiment, the heterologous nucleic acid sequence encodes a therapeutic polypeptide. A therapeutic polypeptide is any polypeptide which can be used to treat a disorder in a subject or cell. Specific, non-limiting examples of therapeutic polypeptides include cytokine and immunomodulators, hormones, and neurotransmitters. In a subject or cell deficient for a specific polypeptide, a therapeutic polypeptide can be that specific polypeptide, can be a variant of that specific polypeptide, or can be another polypeptide that serves the same function in the subject or cell. Specific non-limiting examples of therapeutic polypeptides of use with the invention include, but are not limited to, IL-2, IL-4, IL-6, IL-8, IL-12, TNF-α, TNF-β, and IFN-γ, EPO, growth hormone (GH), alpha anti-trypsin), and alpha-galactosidase A.

The heterologous nucleic acid can also encode an antigen, an antigenic peptide, or a fusion protein including an antigen or an antigenic peptide. Without being bound by theory, transformation of a cell with the retroviral vector results in reconstitution of the nucleic acid encoding the antigen, and expression of the antigen. Subsequent expression of the antigen in a cell in a subject results in the production of an immune response.

The 5' portion of the heterologous nucleic acid sequence can be operably linked to a promoter. In one embodiment, the promoter is a viral promoter, such as a retroviral promoter or a CMV promoter. In another embodiment, the promoter is a non-retroviral promoter, such as a tissue specific promoter. Specific, non-limiting examples of tissue specific promoters are the insulin promoter, the immunoglobulin promoter, and the elastase promoter. In yet another embodiment, the promoter is a tetracycline regulated promoter. In a further embodiment, the promoter is an RNA pol III promoter such as a tRNA promoter.

In a further embodiment of the present invention, the retroviral vector can include a heterologous nucleic acid that encodes an antisense molecule, which includes antigene molecules. Antisense and sense molecules include oligonucleotides that interfere with expression of DNA or RNA. In one aspect of the present invention, the antisense or sense molecules can bind to the target RNA, or otherwise interfere with the translation of the target RNA. In another aspect of the invention, the antisense molecule induces Rnase H-mediated RNA degradation, or inhibits RNA polymerase II. In another aspect of the invention, the antisense molecule binds to the target DNA and disrupts transcription.

For instance, antisense or antigene molecules can have complementary nucleotide sequences to the target DNA or RNA. These complementary nucleotide sequences can specifically hybridize to the target DNA or RNA by Watson-Crick base pair formation or Hoogsteen base pair formation.

Expression of the heterologous nucleic acid in transfected cells can be evaluated by a variety of techniques including spectrophotometric assays, ELISA, Northern blot and other standard protein assays which allow one to determine that the heterologous nucleic acid is being expressed (for example assaying for the conversion of L-dopa to L-dopamine after transfecting cells with the AADC gene). Transfected cells can be analyzed for cellular RNA by extraction of the RNA by standard methods, and by measurement of absorbance of light at set wavelengths. Northern blot and slot-blot hybridization can be used to quantify RNA.

Kits

The retroviral vectors of the invention are ideally suited for the preparation of a kit. Such a kit may comprise a carrier means, such as a box, bag, or plastic carton, containing one or more container means such as vials, tubes, and the like. Each of the container means can include a separate element to be used in a method. For example, one of the container means can include a retroviral vector of the invention. The kit may also contain a container means with a buffer or vehicle for the introduction of the retroviral vector. In addition, written instructions can be provided to detail the use of the components of the kit.

Without further elaboration, it is believed that one skilled in the art can, using this description, utilize the present invention to its fullest extent. The following examples are illustrative only, and not limiting of the remainder of the disclosure in any way whatsoever.

SPECIFIC EXAMPLES

Example 1

Materials and Methods

Construction of vectors: Plasmids pSR2, pSR5, pSR6, pMS2 were derived from pAR2 (see FIG. 2) (Yin et al., *J. Virol.* 71(3): 2487–2494, 1997) an MLV-based vector that contains hygromycin phosphotransferase B gene (hygro). The terminology used below, refers to several nucleic acid sequences by a specific numeration or name. When the sequence is included in a plasmid, the name of the nucleic acid sequence started is prefaced with the letter "p" (e.g. pSR2). However, when referring to a virus, the name of the nucleic acid sequence does not include the latter "p" (e.g. SR2).

pAR2 was digested to completion with AatII, self-ligated to generate pTR1, a plasmid that contained a portion of hygro and the downstream LTR. A nucleotide sequence encoding green fluorescent protein (GFP) was amplified by PCR using primers GFPp1-AscI and PPG2p-csA. The sequences of the primers used in the amplification reaction are shown below in Table 1.

TABLE 1

Primers used for vector construction and DNA sequence analysis

| Primer name | Primer sequences | |
|---|---|---|
| GFPp1-AscI | 5' TCTCCGAATGGCGCGCCGCCACCATGAGCAAGGGC 3' | (SEQ ID NO:1) |
| PFG2p-csA | 5' CCTATCTCGAGGCGCGCCTCACTTGTACAGCTCGTCCATG-3' | (SEQ ID NO:2) |
| GFPp3-EheI | 5'-ATCCCGAATCGGCGCCGCCACCATGAGCAAGGGC-3' | (SEQ ID NO:3) |
| PFG4p-ehEI | 5'-GTCATGTCAAGGCGCCTCACTTGTACAGCTCGTCCATG-3' | (SEQ ID NO:4) |
| FPAscp1 | 5'-ATATAGGCCTGGCGCGCCATGCCCGAGGGCTATG-3' | (SEQ ID NO:5) |
| FG-ehE-4p | 5'-CGGTAGCAATGGCGCCAACTTGACTTCAGCGCGGGTC-3' | (SEQ ID NO:6) |
| MLVU3 | 5'-ATGTTTCCAGGGTGCCCCAAGGACC-3' | (SEQ ID NO:7) |
| ispVLM5' | 5'-TCAAACCTCGACACTAGACAATCGG-3' | (SEQ ID NO:8) |
| GF101 | 5'-CAGCGGAGAGGGTGAAGGTG-3' | (SEQ ID NO:9) |
| 5UVLM | 5'-TCGTGGGTAGTCAATCACTCAGAGG-3' | (SEQ ID NO:10) |
| R/3UM-629 | 5'CGACGCAGTCTATCGGAAGACT-3' | (SEQ ID NO:11) |

The resulting DNA was digested with AscI and inserted into the AscI site between the U3 and R of the upstream LTR of pAR2 to generate pCM1. GFP was amplified by PCR using primers GFPp3-EheI and PFG4p-ehEI, the amplified product was digested with EheI and inserted into the EheI site between the U3 and R in the LTR in pTR1 to generate pCM2. pCM1 and pCM2 were digested with ScaI, and the DNA fragment from pCM1 containing the upstream LTR with GFP was ligated to the DNA fragment from pCM2 containing the downstream LTR. The resulting plasmid pSR1 contains hygro, and both LTRs have a copy of GFP. pSR1 was digested with BstEII and ClaI to excise hygro, and replaced with the SV40 promoter-hygro fragment from pMSM2 to generate pSR2.

A portion of the GFP containing the 3' 465 base pair (bp) fragment, termed FP, was amplified by PCR using primers FPAscp1 and PFG2pcsA. The PCR product was digested with AscI and inserted into the AscI site in the 5' LTR of pAR2 to generate pTR2. A portion of GFP containing the 5' 353-bp fragment, term GF, was amplified using primers FG-ehE-4p and GFPp3-EheI. The PCR product was digested with EheI and inserted into the EheI site of pTR1 to generate pTR4. The DNA fragment derived from pTR2 containing the upstream LTR with the FP was isolated, similarly the DNA fragment from pTR4 containing the downstream LTR with GF was also isolated. These two DNA fragment were ligated to form pTR5.

pTR5 was digested with BstEII and ClaI to excise hygro and the 1.7-kb DNA fragment containing SV40 promoter-hygro was cloned into pTR5 to generate pSR3. pSR3 was sequenced and an inactivating mutation was found in the GF. To correct this, pCM2 was digested with ClaI and BstBI to excise the 3' hygro, U3 and 'GF' fragment, and ligated into the eluted 6.1 kb backbone of pSR3 that was generated by digestion with ClaI and partially digestion with MscI to generate pSR5. In pSR5, the GF region contained the 5' 358-bp of GFP and the F region that is shared by both GF and FP fragments are 87-bp in length.

Plasmid pSR6 was generated by digesting pAR2 with ClaI and BstEII to excise the 1.4-kb fragment between the ψ and 3' end of hygro and replacing it with the 1.7-kb BstEII-ClaI fragment containing SV40-hygro from pMSM2.

Plasmid pJD220SVhy was digested with ClaI and BstZ17I. A 409-bp DNA fragment containing the SV40 termination signal was eluted. Plasmid pCM2 was digested with BstBI and BstZ17I to delete the 3' 376-bp of GFP, R, and U5. The resulting DNA was treated with the Klenow fragment of E. coli DNA polymerase I and ligated with a 409-bp DNA fragment from JD220SVhy (Dougherty and Temin, Proc. Natl. Acad. Sci. 84:1197–1201, 1987) containing the SV40 termination signal to generate pMS1. Plasmid pMS1 was digested with ScaI and the fragment containing the 3' LTR was eluted and ligated to ScaI digested pSR5 to generate pMS2. Plasmid pMP1 was derived from pWH390 (see Delviks et al., J. Virol. 71(8):6218–6224, 1997) by insertion of GFP upstream of IRES.

Standard cloning techniques were used to construct all of the vectors (see Sambrook et al. (In: *Molecular Cloning: A Laboratory Manual*, Cold Spring Harbor, N.Y., 1989). Plasmid structures were analyzed by restriction enzyme mapping. All PCR-amplified DNA fragments that were cloned into plasmids were further analyzed by DNA sequencing to avoid inadvertent mutations generated during the PCR procedures.

Cell Culture, DNA transfection, and virus infection: PG13 cells (American Type Culture Collection (ATCC) No. CRL-10686) are derived from NIH3T3 cells that express MLV gag-pol and gibbon-ape leukemia virus (GaLV) env. D17 (American Type Culture Collection (ATCC) No. CRL-6248) is a dog osteosarcoma cell line permissive for MLV infection.

PG13 and D17 cells were maintained at 37° C. in Dulbecco's modified Eagle's media (DMEM) supplemented with penicillin (50 U/ml; Gibco), streptomycin (50 µg/ml; Gibco), and bovine calf serum (10% for PG13 and 6% for D17). G418, a neomycin analog, was used for selection at a final concentration of 900 µg/ml in PG13 cells and 600 µg/ml in D17 cells. Hygromycin was used at a final concentration of 600 µg/ml in PG13 cells and 240 µg/ml in D17 cells.

Transfections were performed using the $CaPO_4$ precipitation method as previously described (Sambrook et al., *Molecular Cloning: A Laboratory Manual*, Cold Spring Harbor, N.Y., 1989) or Transfast™ transfection reagents from Promega as recommended by the manufacturer. PG13 cells were plated at a density of $1 \times 10^5$ cells per 60-mm-dish; 5 or 10 µg of vector DNA was used per dish for the Transfast™ or calcium phosphate transfection, respectively. Transfected cells were placed on appropriate drug selections; drug resistant colonies were pooled, expanded, and plated at a density of $5 \times 10^6$ cells per 100-mm-dish. Viruses were harvested from each transfected cell pools 48 h later, centrifuged at 3000×g for 10 min to remove cellular debris, and serially diluted. These viruses were used to infect D17 cells that were plated at $2 \times 10^5$ cells per 60-mm-dish. Infected D17 cells were placed on appropriate drug selection. Viral titers were calculated based on the number of drug-resistant colonies and standardized to the reverse transcriptase activities.

Reverse transcriptase (RT) Assay: A portion of virus harvested from transfected cells was subjected to reverse transcriptase assays, as previously described (Halvas et al., J. Virol. 74(1):312–319, 2000). Briefly, harvested virus was centrifuged in an SW41 rotor at 25,000 RPM for 90 minutes. Viral pellets were resuspended in serum-free media and stored at −80° C. Exogenous reverse transcriptase activities were determined by incubating 10 µl of virus with 50 µg/ml of (20-mer) oligo (T) (Integrated DNA Technologies, Coralville, Iowa), 100 µg/ml of poly (A) (Pharmacia, Piscataway, N.J.), 0.03 M NaCl, 0.25 M Tris, 0.01U/µl RNase Inhibitor, 0.005 M dithiothreitol, $3 \times 10^{-4}$ M $MnCl_2$, 0.04 mM dTTP, $2.5 \times 10^{-3}$ µl IGE Pal (Sigma, St. Louis, NO), and 10 µCi of [$^3$H] dTTP. The samples were incubated at 37° C. for 90 min. The reaction mixtures were precipitated with 10% trichloroacetic acid (Sigma) and filtered through 0.45-µm-pore-size Metricel membranes (Gelman Sciences, Inc., Ann Arbor, Mich.), and the amount of [$^3$H] incorporated was determined using a scintillation counter.

Detection of GFP expression by flow cytomety and fluorescence microscopy: The number of cells in the transfected pools that expressed GFP were measured using flow cytometry (FACScan, Becton Dickenson). Results were analyzed using the CellQuest software (Becton Dickenson, Bedford, Mass.). GFP expression in infected, drug-resistant D17 cells were analyzed by two methods. Drug-resistant cell colonies from $10^0$, $10^{-1}$, and $10^{-2}$ virus dilution plates were separately pooled for flow cytometry analyses. Drug-resistant colonies from the $10^{-3}$, $10^{-4}$, and $10^{-5}$ plates were analyzed for fluorescence by microscopy using a FITC 505 nm long-pass filter (Axiovert Inverted fluorescence microscope, Zeiss, Thornwood, N.Y.). GFP expression in individual cell clones was also analyzed by flow cytometry or microscopy.

Analyses of proviral structure by PCR and DNA sequencing: Hygromycin-resistant cell clones were isolated and lysed. These lysates were used as substrates for PCR. The upstream LTR of the proviruses was amplified using primers in the U3 (MLVU3) and 5' ψ regions (ispVLM5'). PCR products were analyzed by DNA sequencing with an automated sequencer (PE biosystems, Foster City, Calif.) using one or more of the following primers, GF101, 5UVLM, and R/3UM-629.

Example 2

Production of Vectors to Evaluate Minus-strand DNA Transfer

Figure 2:
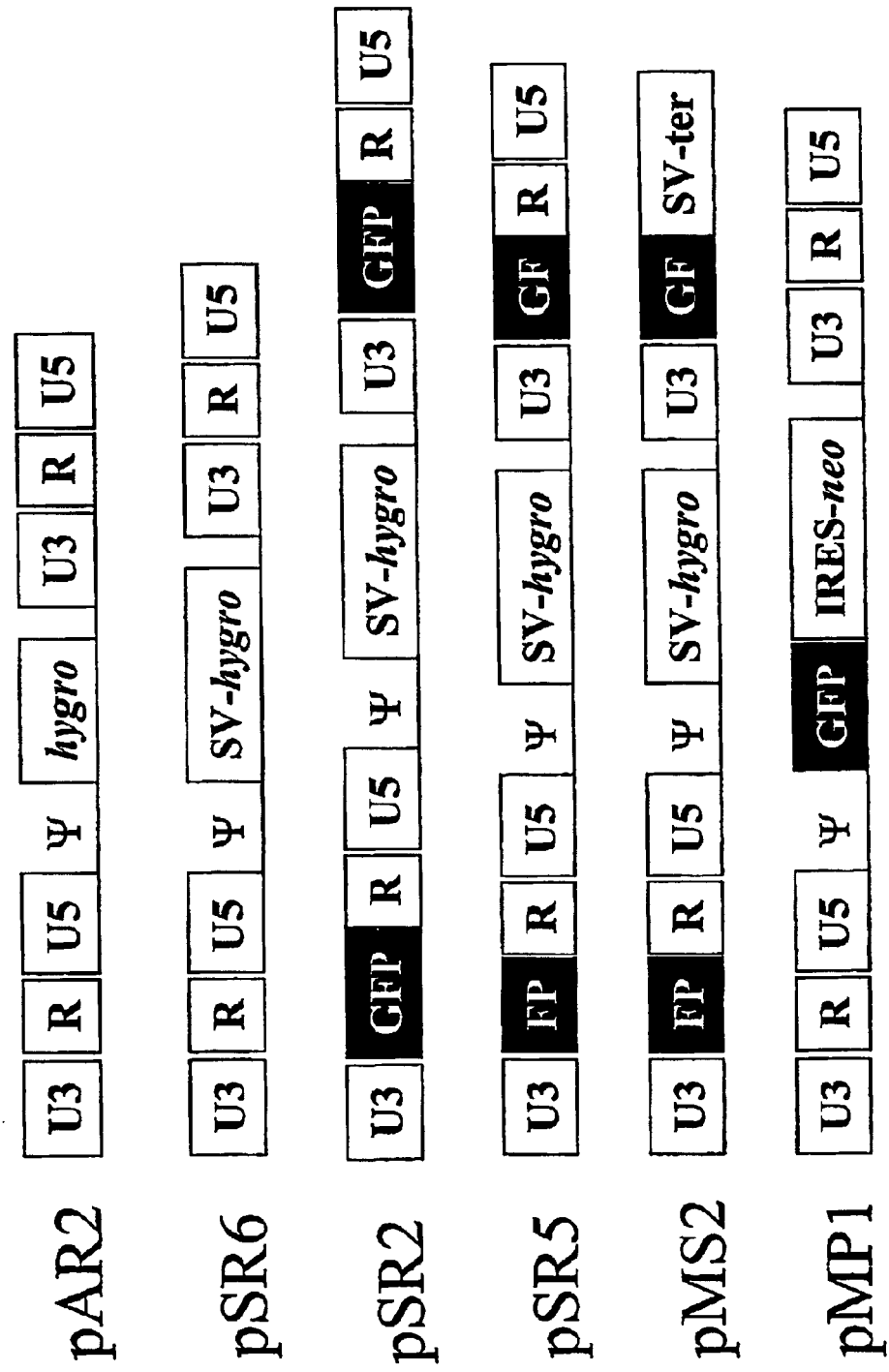
FIG. 2 is a schematic diagram of retroviral constructs including a heterologous nucleic acid (green fluorescent protein, GFP). "SV40-ter" is the SV40 termination signal. "SV-hygro" is nucleic acid encoding a promoter and a hygromycin resistance gene. "ψ" is a packaging signal.

A series of MLV-based retroviral vectors were constructed evaluate the reconstitution of genes using minus-strand DNA transfer. The structures of these vectors are shown in FIG. 2. The vectors used in these experiments contained cis-acting sequences necessary for the retroviral replication such as primer binding site, packaging signal (ψ$^+$), polypurine tract, and attachment (att) sites. Most of the gag, all of the pol, and the entire env were deleted from these vectors.

Vector pAR2 contained two unmodified LTRs with hygro between the LTRs. Vectors pSR2, pSR5, pSR6, and pMS2 each contained an SV40 promoter upstream of hygro between the two LTRs. Vectors pSR6 contained two unmodified LTRs; pSR2 contained two modified LTRs each had a full-length GFP that was inserted between U3 and R. pSR5 had two modified LTRs, the upstream LTR contained the 3' 465-bp of GFP (termed FP) between U3 and R, whereas the downstream LTR contained the 5' 353-bp of GFP (termed GF) between U3 and R. FP and GF share a stretch of 87-bp homology (the "F" region). pMS2 also had two modified LTRs similar to those in pSR5 except that the R and U5 regions in the downstream LTR were replaced by a DNA fragment containing the SV40 termination signal. Vector pMP1 contained two unmodified LTRs with GFP, internal ribosomal entry site (IRES) from encephalomyocarditis_virus, and neomycin phosphotransferase gene (neo) between the LTRs.

Figure 3:
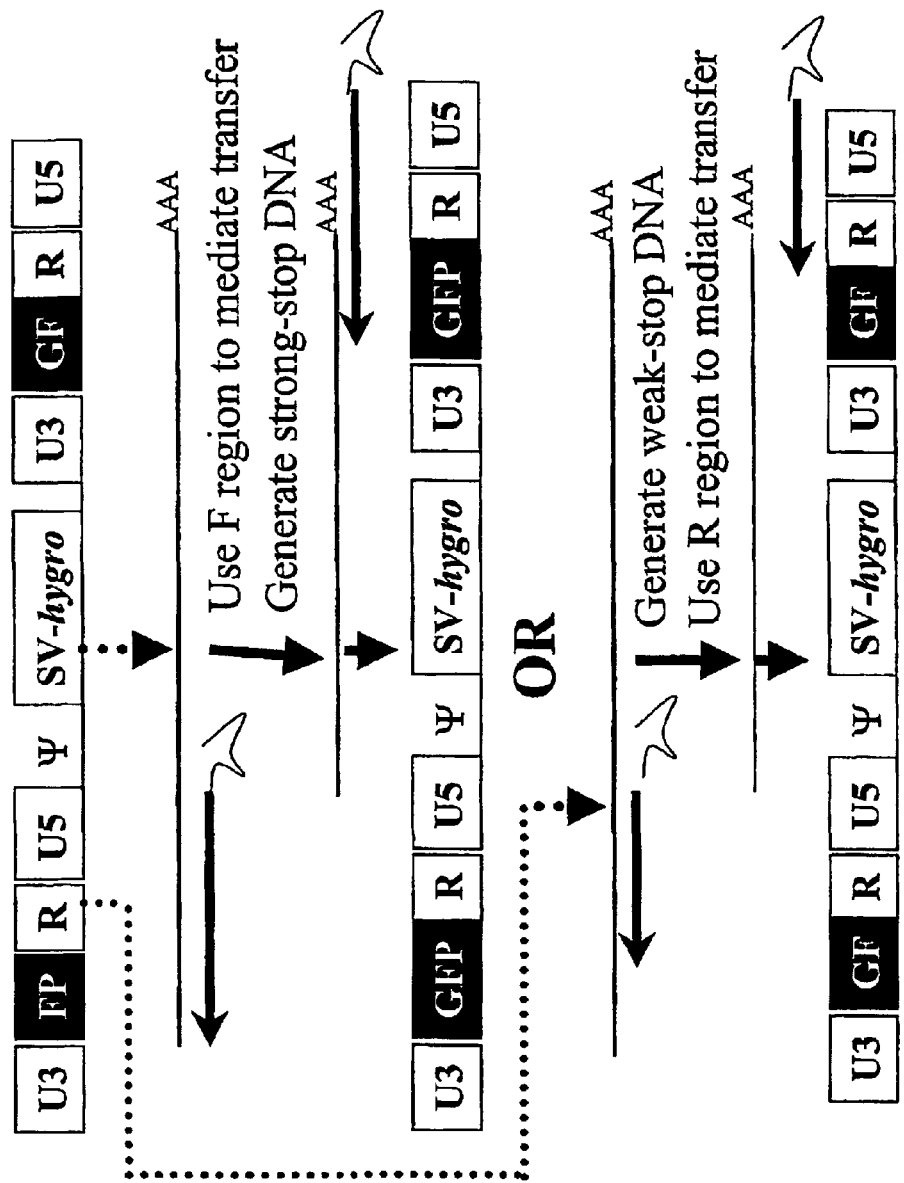
FIG. 3 is a schematic diagram showing the use of pSR5 to reconstitute and duplicate GFP nucleic acid after the introduction of pSR5 in a host cell.
Figure 4:
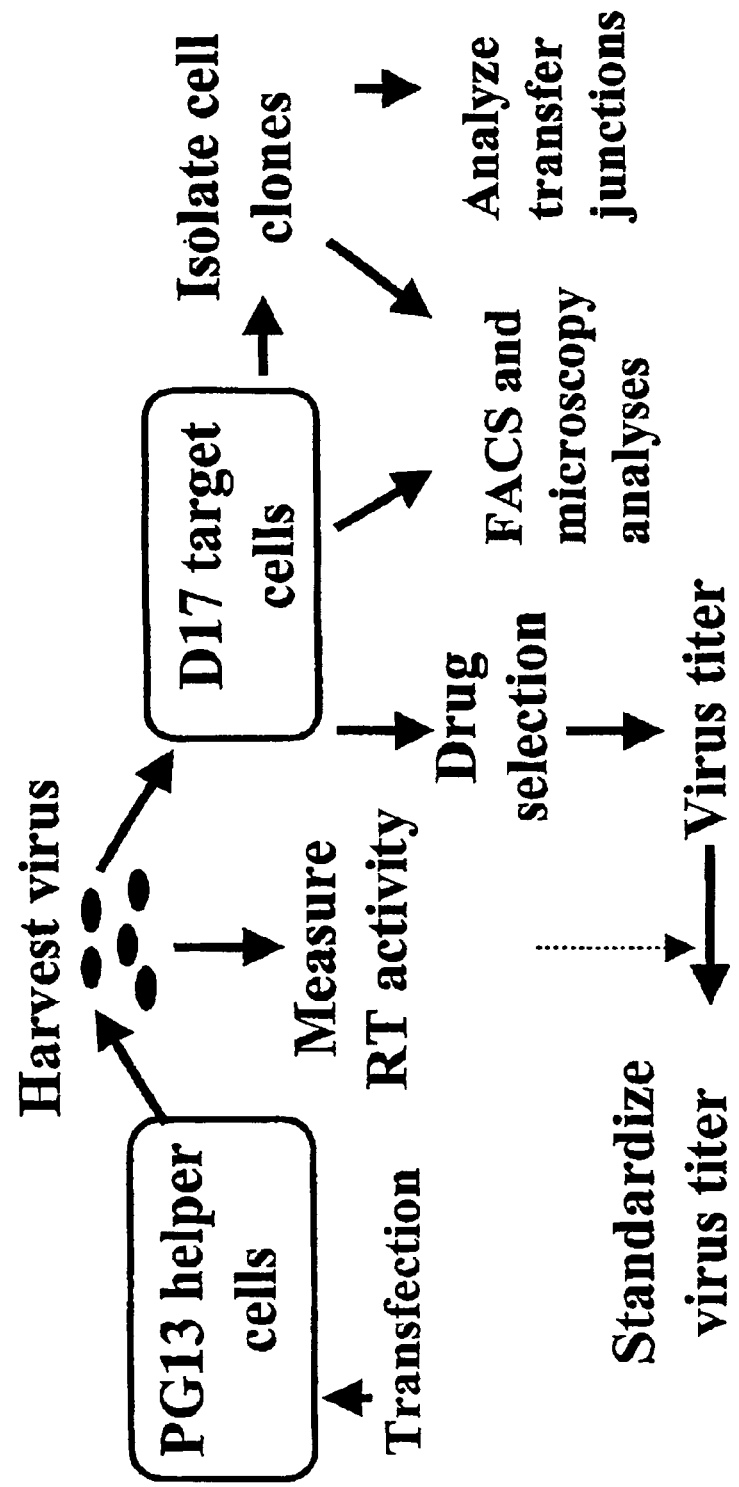
FIG. 4 is a schematic diagram of the experimental methods used to document the use of pSR5 to reconstitute and duplicate GFP nucleic acid.

AR2, SR6, and MP1 contained unmodified LTRs and were expected to produce RNAs with R at the two ends of the viral sequences that could mediate minus-strand DNA transfer. The LTRs in pSR5 were modified, as a result, the viral RNA produced would contained FP-R-U5 at the 5' end and U3-GF-R at the 3' end of the viral sequences (FIG. 3). Without being bound by theory, during reverse transcription, DNA synthesis will copy U5, R, and FP to form minus-strand strong-stop DNA (FIG. 2). As non-viral sequences can mediate minus-strand DNA strand transfer, then the F region (87-nt) in the strong-stop DNA hybridizes to the F region at the 3' end of viral RNA, reverse transcription continues to copy the G region of the RNA, and GFP is reconstituted. It is also known that at a lower frequency, approximately 10–15% of the time, minus-strand DNA synthesis terminates early to form weak-stop DNA; this DNA contains only U5 and R. These weak-stop DNAs should be able to transfer to the 3' end of viral RNA. DNA synthesis will then continue to form viral DNA containing GF between U3 and R. During this process, a copy of viral DNA that is capable of integration would be generated; however, the GFP gene would not be reconstituted.

The LTRs in pMS2 were modified similar to pSR5 except that the R and U5 were deleted from the 3' LTR. Thus, the MS2 viral RNA also has FP-R at the 5' end and U3-GF at the 3' end of the viral sequences; however, the viral RNA does not contain R at the 3' end. If the F region can mediate minus-strand DNA transfer, then the strong-stop DNA can transfer to the 3' end of the viral RNA sequences. However, unlike SR5, the weak-stop DNA only containing U5 and R would not have complementarity with the sequences at the 3' end of the viral RNA, and would not be able to transfer efficiently. Therefore, if the F region could not mediate efficient minus-strand DNA transfer, it was expected that MS2 would not be able to replicate well and would have a severely reduced viral titer. This virus served as a positive control.

The LTRs in pSR2 each contained a copy of GFP between the U3 and R. the RNA produced from these constructs should contain GFP-R-U5 at the 5' end and U3-GFP-R at the 3' end of the viral sequences. Whether the virus used the R region or the non-viral sequences to mediate minus-strand transfers, the resulting viral DNA would have LTRs with GFP between U3 and R sequences. As MS2 replicated well (see below), the F region mediated minus strand transfer.

A diagram of the experimental protocol utilized for the experiments described below is shown in FIG. 3. These vectors were separately transfected into PG13 helper cells that expressed MLV gag-pol and GaLV env. Transfected cells were placed on appropriate drug selection, and resistant cell colonies were pooled. All of the pools contained at least 250 colonies. Viruses were harvested from these pools; for each sample, a portion of the virus was used to measure the RT activity and a portion of the virus was serially diluted and used to infect D17 cells. Infected D17 cells were placed on appropriate drug selection. The numbers of drug-resistant colonies were determined and were used to calculate viral titers generated by these vectors. GFP expression from these drug-resistant colonies was analyzed by flow cytometry or fluorescence microscopy. Infected, drug-resistant D17 cell clones were isolated; GFP expression of these cell clones was determined by fluorescence microscopy and flow cytometry analyses. To examine the molecular nature of the minus-strand DNA transfer, a portion of the proviruses containing minus-strand DNA transfer junctions were amplified from the infected cell clones by PCR and characterized by DNA sequencing.

In this system, virus titers and minus-strand DNA transfers were examined from the viruses produced in the PG13 cells and the proviruses generated in the D17 cells. PG13 cells were derived from murine cells; the viruses produced from PG13 contained GaLV Env that could not efficiently infect murine cells. Therefore, reinfection had little opportunity to occur in these cells. D17 cells did not express gag-pol and env needed to produce virions containing these vectors to go through another round of viral replication. Therefore, only one round of retroviral replication was allowed in this system.

Virus titers after one round of retroviral replication: The titers for vectors AR2, MP1, SR2, SR5, and MS2 are listed in Table 2.

TABLE 2

| | Virus titers generated by PG13 cells transfected with vector plasmids | | | | |
|---|---|---|---|---|---|
| Exp. # | MP1 × $10^4$ | SR6 × $10^4$ | SR2 × $10^4$ | SR5 × $10^4$ | MS2 × $10^4$ |
| A | 72 | 12 | ND | 2.6 | 1.3 |
| B | 44 | 19 | 4.9 | 1.0 | 4.7 |
| C | 16 | 8.3 | 4.1# | 13 | 11 |
| D | 43 | 17 | 5.9 | 4.0 | 3.2 |
| E | 130 | 130 | 14 | 24 | 21 |

*Within each set of experiment, the virus titers (CFU/ml) were standardized to RT activities. In general, within each set of experiment, RT activities were within 20% differences between samples.
This titer measurement was not standardized to RT activity.

Virus titers after one round of retroviral replication: The titers for vectors MP1, SR2, SR5, SR6, and MS2 are listed in Table 2. These titers were standardized to RT activities. The titer for SR6 varied between $8.3 \times 10^4$ and $130 \times 10^4$ colony forming units per ml (CFU/ml). The titer for SR5 varied between $2.6 \times 10^4$ to $24 \times 10^4$ CFU/ml. The average difference between SR6 titers and SR5 titers was 6.8-fold. The reductions in viral titers could be caused by inserting sequences in the LTRs, similar to the 6- to 8-fold decreases in titers previously observed from another laboratory (Adam et al., Human Gene Therapy 6:1169–1176, 1995). Alternatively, it was possible that the F region could not mediate the minus-strand DNA transfer and caused the decrease in the viral titer. This would suggest that most of the minus-strand strong-stop DNA could not perform strand transfer and did not produce viral DNA capable of integrating into the host genome. Most of the viral titer would be generated from viral DNA produced by the transfer of minus-strand weak-stop DNA. Since the weak-stop DNA was expected to be generated approximately 10% of the time, it would correlate with the approximately 6.8-fold decrease in viral titers.

Alternatively, it was possible that the F region could not mediate the minus-strand DNA transfer and caused the decrease in the viral titer. This would suggest that most of the minus-strand strong-stop DNA could not perform strand transfer and did not produce viral DNA capable of integrating into the host genome. Most of the viral titer would be generated from viral DNA produced by the transfer of minus-strand weak-stop DNA. Since the weak-stop DNA was expected to be generated approximately 10% of the time, it would correlate with the approximately 10-fold decrease in viral titers.

The titers for SR2 and MS2 varied from $4.1 \times 10^4$ to $14 \times 10^4$ CFU/ml and $1.3 \times 10^4$ to $21 \times 10^4$ CFU/ml, respectively. There was no significant difference between SR2, SR5, and MS2 titers. MS2 RNA only contained the 5' R and therefore could not use R to mediate minus-strand DNA transfer. Therefore, in order for MS2 to generate similar viral titers as SR2 and SR5, the F region had to be able to mediate minus-strand DNA transfer. The proviruses generated by F region-mediated transfer would have reconstituted GFP, which could be confirmed by GFP expression or structural analyses.

Example 3

Confirmation of F Region-Mediated Transfer: GFP Expression in Transfected and Infected Cells GFP expression in all of the transfected cell pools was examined by FACS analyses. As expected, pMP1- or pSR2-transfected, drug-resistant cell pools contained significant numbers of GFP-expressing cells, generally between 45–70%. As expected, cell pools transfected with pAR2 or pSR6 did not contained a significant percentage of fluorescent cells (less then 2%) since these plasmids lack GFP. Cell pools transfected with pSR5 or pMS2 also did not contained a significant percentage of fluorescent cells (less than 2%), indicating that neither FP nor GF fragment could express fluorescent proteins.

Flow cytometry analyses were also performed on D17 cells infected with virus produced by different transfected cell pools. Drug-resistant D17 cells were pooled and were analyzed by flow cytometry; these data are summarized below in Table 3.

TABLE 3

Percent of infected D17 cells that were positive in GFP expression by FACS analyses[1]

| Exp. # | MP1 | SR6 | SR2 | SR5 | MS2 |
|---|---|---|---|---|---|
| A | 70.1% | 0.1% | ND | 69.9% | 89.8% |
| B | 84.1% | 0.5% | 98.0% | 65.0% | 91.3% |
| C | 85.6% | 0.6% | 98.0% | 78.1% | 88.4% |
| D | 78.2% | 0.1% | 97.6% | 76.0% | 95.2% |
| E | 80.1% | 0.1% | 97.1% | 75.5% | 93.7% |
| Mean ± SE | 79.6 ± 2.7% | 0.3 ± 0.1% | 97.7 ± 0.2% | 72.9 ± 2.4% | 91.7 ± 1.2% |

[1]For each infection, three pools of cells infected with different viral dilutions were analyzed, the numbers of GFP-positive cells were averaged and shown in the table.

GFP expression of infected cells: Flow cytometry analyses were also performed on D17 cells infected with virus produced by different transfected cell pools. Drug-resistant D17 cells were pooled and were analyzed by flow cytometry; these data are summarized in Table 3. MP1 and SR2 both contained intact GFP; most of the D17 cells infected with these two viruses were positive for GFP expression, with an average of 80% and 98%, respectively. SR6 did not contain GFP; very few infected D17 cells were positive for GFP expression when analyzed by flow cytometry (average of less than 0.3%). In all experiments, a high proportion of cells infected with SR5 were positive in GFP expression, ranging from 65% to 78.1% with an average of 72.9% (Table 3). Most of the cells infected with MS2 were positive for GFP expression, the percentage ranging from 88.4 to 95.2% with an average of 91.7%. These experiments demonstrated that, most of the time, GFP was reconstituted during reverse transcription of SR5 and MS2 RNA. Therefore, the F region was used to mediate minus-strand DNA transfer during reverse transcription of these proviruses.

In addition to the flow cytometry analyses, GFP expression of the cell colonies was also examined using fluorescent microscopy. As expected, GFP expression was found in 0 of 369 SR6-infected colonies (>0.1%). GFP expressions were found in 667 of 828 (80.6%) MP1-infected colonies, 305 of 341 (89.4%) SR2-infected colonies, 629 of 856 (73.5%) SR5-infected colonies, and 1002 of 1092 (91.8%) MS2-infected colonies. The frequencies of GFP expression detected by the microscopy were similar to those observed by flow cytometry analyses.

Example 4

Molecular Characterization of the Minus-strand DNA Transfer in SR5 and MS2

Figure 5:
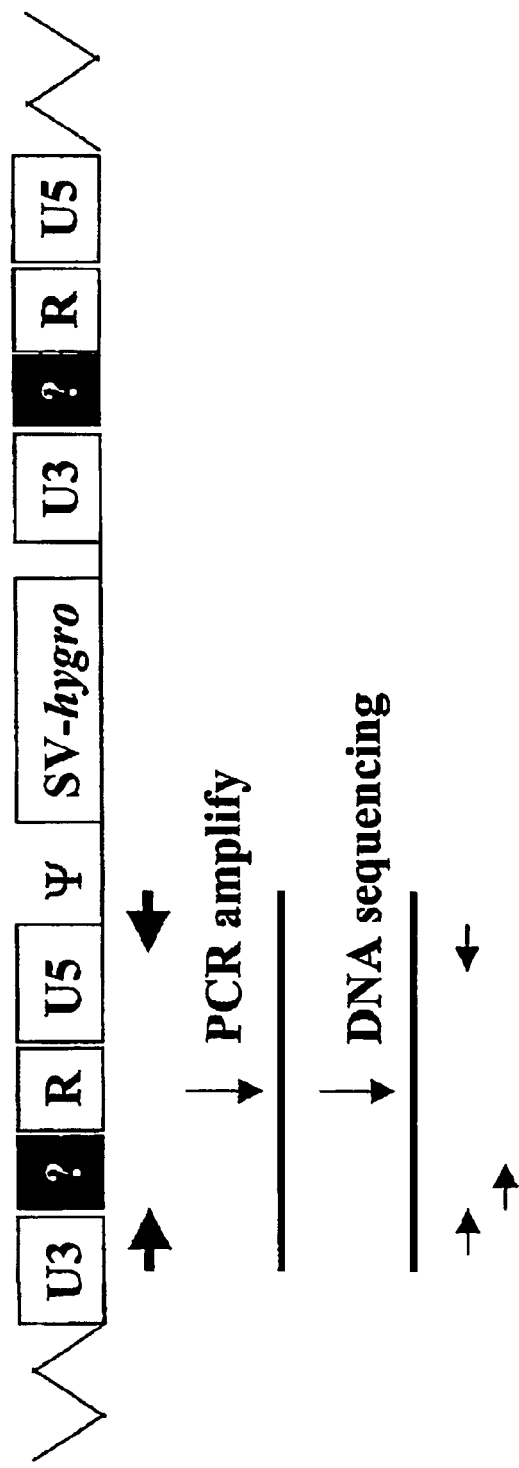
FIG. 5 is a schematic diagram of the experimental methods used to determine the sequence of reconstituted heterologous nucleic acid integrated into a cellular genome using the methods described herein.

To directly analyze the molecular nature of minus-strand DNA transfer, drug-resistant cell clones were isolated. A portion of the proviral genome containing the upstream LTR was amplified and sequenced to characterize the molecular nature of the transfer events (FIG. 5).

Partial proviral structures from 13 SR5-infected cell clones were characterized; of the 13 clones, 4 expressed GFP and the other 9 were negative in GFP expression by fluorescent microscopy and flow cytometry analyses. All of the four proviruses that expressed GFP contained the expected structures and had U3-reconstituted GFP-R and U5 in the LTRs. None of the 9 proviruses that did not express GFP had the reconstituted GFP in their LTRs. Six of the 9 proviruses had U3-GF-R-U5 in the LTRs (FIG. 3).

Three of the 9 proviruses had U3-FP-R-U5 in their LTRs; these were likely to be the generated from read-in transcripts. It was hypothesized that in the virus producing cells, some transfected pSR5 might integrate close to promoters. RNA transcripts initiating from the promoter upstream of U3, termed "read-in transcripts," would contain the upstream U3 sequences along with FP, R, and U5. During reverse transcription, minus-strand DNA synthesis would copy U5, R, FP, and a portion of U3. The complementarity between the newly synthesized U3 DNA and U3 near the 3' end of RNA could be used to mediate minus-strand DNA transfer. The resulting provirus would have 2 LTRs containing U3, FP, R, and U5.

The molecular nature of the minus-strand DNA transfer was also examined in 12 MS2-infected cell clones. Of the 12 cell clones, 9 were positive and 3 were negative for GFP expression by both fluorescent microscopy and flow cytometry analyses. Similar to the clones from SR5, all of the 9 proviruses that expressed GFP had precisely reconstituted GFP in their LTRs. Of the 3 proviruses that did not express GFP, one had a reconstituted GFP that contained a G to C substitution mutation in the G region that converted a glycine to an arginine residue to inactivate the GFP. The other two proviruses had U3-FP-R-U5 structure in the LTR similar to those in SR5; which were presumably generated from read-in transcripts.

Analyses of GFP expression in the SR5 and MS2 infected cell populations indicated that GFP was reconstituted at approximately 73% and 92% efficiency, respectively. Molecular characterization of 13 GFP-expressing proviruses generated from SR5 or MS2 demonstrated that these proviruses contained precisely reconstituted GFP, indicating that the F region was used to mediate minus-strand DNA transfer in these viruses. In one round of replication, MS2 generated similar titers as SR5 and SR2, which could use both R or F regions to mediate minus-strand DNA transfer. This demonstrated that eliminating the R homology did not significantly reduce viral titers. These data demonstrated that the F region can be used to mediate minus-strand DNA transfer in an efficient manner. In addition, it was demonstrated that minus-strand DNA transfer could be used as an effective means to reconstitute and produce duplicated copies of nucleic acid sequences during virus replication.

Example 5

A Short Stretch f Repeat can Mediate Strand Transfer

Figure 7:
FIG. 7 is a schematic diagram of a hybrid MLV/SNV retrovirus.

A set of experiments was performed to demonstrate that short stretches of homology can be used to mediate transfer. Thus, in order to examine whether minus-strand transfer can occur between two R sequences without any significant homology, the LTR from MLV at the 5' end and the LTR from spleen necrosis virus at the 3' end were used in viral constructs. The R regions of these two viruses does not contain significant homology. The construct is shown in FIG. 7.

This virus was found to replicate at a low titer, between $0.6 \times 10^2$ to $3.6 \times 10^2$ CFU/ml. When the provirus generated was examined, it was determined that viruses used short repeats to mediate minus-strand transfer. Of the 13 proviruses examined, 10 used a 6-nt homology, one used a 1-nt homology, and 2 used a 8-nt homology in U3 of SNV and R of MLV (see Yin et al., 1997, Journal of Virology 71:2487–2494, herein incorporated by reference). Thus, a small region of homology, from about 6 to about 8 nucleotides in length, can be used to mediate minus-strand DNA transfer, and thus can be used to reconstitute and duplicate a nucleic acid sequence of interest.

Example 6

Investigation of the Extent of Homology Required to Mediate Efficient Transfer

Figure 8:
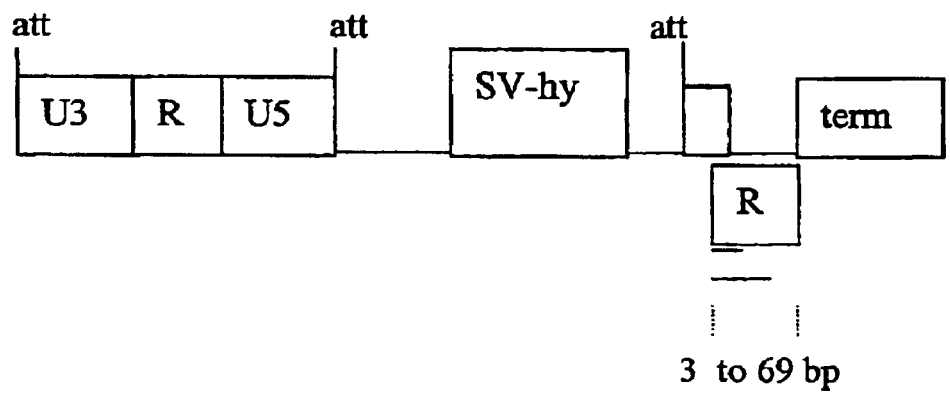
FIG. 8 is a schematic diagram showing the generation of retroviral vectors including an SV40 promoter and a hygromycin resistance gene.

A series of vectors were designed that have the 5' LTR, SV40 promoter and hygromycin resistance gene, but are deleted for the 3' LTR. All of these vectors had the 3' LTR deleted, but still had the attachment sites. It should be noted that in these vectors the U3 promoters and U5 were deleted, and a transcription termination signal was inserted. Between the att and termination signal(s) were placed various lengths of R for each of the different vectors. Thus five vectors were generating containing either 3-, 6-, 12-, 24-, and 69-bp of the R region. The vectors were generated as shown in FIG. 8.

Figure 6:
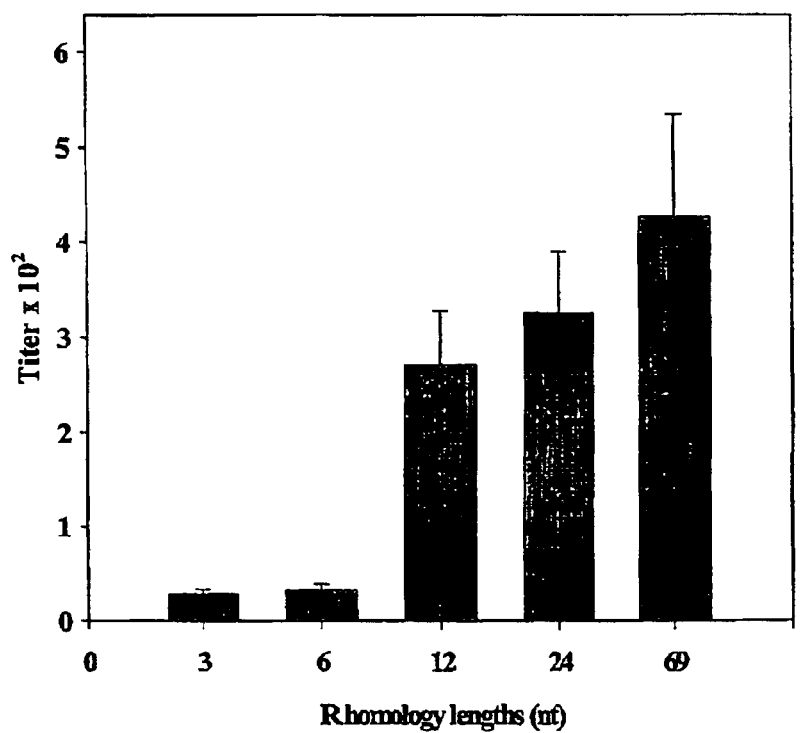
FIG. 6 is a bar graph of viral titers obtained using different lengths (0, 3, 6, 12, 24, and 69 nucleotides) of homology in a terminal repeat of a retrovirus.

Viral replication was then assessed for each of these constructs. Efficient viral replication was observed when 12 base pairs of the R region were included in the construct (FIG. 6). Molecular analyses of the provirus structures also indicated that 12-bp is the threshold for efficient and accurate transfer (see Table 4 below).

TABLE 4

Molecular nature of the minus-strand DNA transfer

| | # of provirus analyzed | # of R—R transfer | # of other transfer |
|---|---|---|---|
| 3-nt | 12 | 0 | 12 |
| 6-nt | 12 | 3 | 9 |
| 12-nt | 11 | 10 | 1 |
| 24-nt | 15 | 15 | 0 |
| 69-nt | 14 | 12 | 2 |

The results demonstrate that viruses with 3 bp homology did not replicate as well and the transfers were not accurate from R to R. Viruses with 6-bp homology performed the correct R- to R transfer in 3 out of 12 proviruses analyzed. Viruses with 12-bp homology performed the correct R to R transfer performed the correct R to R transfer in 10 out of 11 proviruses analyzed. Viruses with 24- or 69-bp homology replicated slightly better than viruses with 12-bp homology; however, the difference is not significant. The majority of the viruses with at least 12 bp homology (12-, 24- or 69-bp homologies) were also transferred accurately from R to R.

Heterologous nucleic acid sequences can thus be used to mediate efficient minus-strand DNA transfer (see Example 6). During the minus-strand DNA transfer process, genes or heterologous nucleic acid sequences can be reconstituted efficiently (up to 90% per replication cycle) using relatively short stretch of homology (e.g., 87-nucleotides). It should be noted that sequences can be efficiently deleted as well (e.g. see U.S. Pat. No. 5,714,353; U.S. Pat. No. 5,741,486, herein incorporated by reference). These sequences include sequences needed for viral replication (such as packaging signal) and antibiotic resistance gene markers or other markers (such as neo and hygo or GFP).

Example 7

Testing Retroviral Vectors in Disease Models In Vivo

The retroviral vectors described in the above examples can be tested for their ability to express a heterologous nucleic acid sequence in mouse models which have been generated for various diseases. Mice which are functionally deleted for a nucleic acid sequence, are infected with a retroviral vector, as described herein. Following infection, minus strand DNA transfer results in the reconstitution of the heterologous nucleic acid. Mice are then screened for their ability to express the heterologous nucleic acid sequence, and the ability of the heterologous nucleic acid sequence to correct the phenotypic affect of the heterologous nucleic acid sequence deletion.

Example 8

Antisense

In one embodiment, the retroviral vector for gene reconstitution and duplication includes an antisense molecule as the heterologous nucleic acid sequence. In general, the reconstituted antisense molecule must by able to bind complementarily to the target RNA. Complementary binding occurs when the base of one molecule forms a hydrogen bond with another molecule. Normally the base Adenine (A) is complementary to thymidine (T) and uracil (U), while cytosine (C) is complementary to guanine (G). Therefore, the sequence 5'-TCGT-3' of the antisense molecule will bind to ACUC of the target RNA, or 5'-ACTC-3' of the target DNA. Additionally, in order to be effective, the antisense and sense molecules do not have to be 100% complementary to the target RNA or DNA.

The antisense polynucleotides can vary in length. Generally, a longer complementary region will give rise to a molecule with higher specificity. When the retroviral vector is introduced into a host cell, the host cell supplies the necessary components for transcription of the therapeutic antisense molecule.

Catalytic nucleic acid and other oligomeric molecules can be designed which degrade target sequences and included in a hybrid adenoviral vector of the invention. Such catalytic antisense molecules can contain complementary regions that specifically hybridize to the target sequence, and non-complementary regions which typically contain a sequence that gives the molecule its catalytic activity.

A particular type of catalytic nucleic acid antisense molecule is a ribozyme or anti-sense conjugates, which may be used to inhibit gene expression (e.g. see PCT publication WO 9523225, and Beigelman et al. *Nucl. Acids Res.* 23:4434–4442, 1995). Examples of oligonucleotides with catalytic activity are described in WO 9506764, WO 9011364, and Sarver et al., *Science* 247:1222–1225, 1990.

The relative ability of an oligomer such as a polynucleotide to bind to a complementary strand is compared by determining the melting temperature of a hybridization complex of a polypeptide and its complementary strand. The melting temperature ($T_m$), a characteristic physical property of double helices, denotes the temperature in degrees Centigrade at which 50% helical versus coiled (unhybridized) forms are present. Base stacking, which occurs during hybridization, is accompanied by a reduction in UV absorption (hypochromicity). A reduction in UV absorption indicates a higher $T_m$. The higher the $T_m$ the greater the strength of the binding of the hybridized strands. As close to optimal fidelity of base pairing as possible achieves optimal hybridization of a polynucleotide to its target RNA.

Example 9

Gene Therapy Using Retroviral Vectors

The present invention provides for the transformation of cells in vitro and in vivo. The nucleic acids can be transfected into cells by packaging the retroviral vector in an viral particle.

In one particular class of embodiments, retroviral vectors are used in cell transformation procedures for gene therapy. Gene therapy provides methods for combating chronic infectious diseases such as HIV, as well as non-infectious diseases such as cancer and birth defects such as enzyme deficiencies.

A new gene therapy approach for patients using the retroviral vectors taught by the present invention, is now made possible. Essentially, cells can be removed from a subject having deletions or mutations of a gene, and then the hybrid retroviral vector (which contains heterologous nucleic acid designed to replace or substitute for the mutated or deleted gene) is introduced into the cell. These transfected cells will thereby have the heterologous nucleic acid reconstituted and duplicated in their genome. These cells can be reintroduced into the patient. Methods described in U.S. Pat. No. 5,162,215 (Bosselman et al.) demonstrate how to detect the presence and expression of a gene of interest in target cells. Methods described in U.S. Pat. No. 5,741,486 (Pathak et al.) teach the use of viral vectors in gene therapy. Such methods can be applied to the retroviral vectors of the present invention, for example in gene therapy.

In addition, the retroviral vectors can be introduced into a subject in vivo. The scientific and medical procedures required for human cell transfection are now routine procedures. The provision herein of a new type of retroviral vectors now allows the development of human and non-human gene therapy based upon these procedures.

In some embodiments, the present invention relates to a method of treating patients which under-express a gene, or in which greater expression of the gene is desired. These methods can be accomplished by introducing a heterologous nucleic acid coding for the under-expressed gene product into a retroviral vector. A vector as described herein is introduced into cells of the patient, and the heterologous nucleic acid is reconstituted and duplicated in the cells of the patient.

In some of the foregoing examples, it may only be necessary to introduce the genetic or protein elements into only certain cells or tissues. However, in some instances (i.e. tumors), it may be more therapeutically effective and simple to treat all of the patients cells, or more broadly disseminate the vector, for example by intravascular administration.

The retroviral vectors can be administered to the patient by any method which allows the vectors to reach the appropriate cells. These methods include injection, infusion, deposition, implantation, or topical administration. Injections can be intradermal or subcutaneous.

In addition, the retroviral vector can be designed to use different promoters to express the heterologous nucleic acid sequence. In one embodiment, the retroviral LTR sequence can serve as a promoter for expression of the transgene. Thus, in one example, a therapeutic nucleic acid is placed under the control of the retroviral LTR promoter. In another embodiment, the heterologous nucleic acid sequence is operatively linked to a heterologous promoter (e.g. the CMV promoter). In yet another embodiment, the heterologous nucleic acid sequence is operatively linked to a tissue specific promoter (e.g. the immunoglobulin promoter), such that the expression of the polypeptide encoded by the heterologous nucleic acid sequence occurs only in a tissue of interest.

Ex Vivo Transformation of Cells

Ex vivo methods for introducing a retroviral vector in a cell in an organism involve transducing the cell ex vivo, and then introducing the cell into the organism. For example, retroviral particles including retroviral capsid proteins and a retroviral vector of the invention can be used to treat autologous cells isolated from a subject. In one embodiment, the cells are lymphocytes, macrophages or stem cells isolated or cultured from a subject. Alternatively, the cells can be heterologous cells such as those stored in a cell bank (e.g., a blood bank).

In one specific non-limiting example, the cells are T cells. Several techniques are known for isolating T cells. In one method, Ficoll-Hypaque density gradient centrifugation is used to separate PBMC from red blood cells and neutrophils according to established procedures. Cells are washed with modified AIM-V [which consists of AIM-V (GIBCO) with 2 mM glutamine, 10 µg/ml gentamicin sulfate, 50 µg/ml streptomycin) supplemented with 1% fetal bovine serum (FBS)]. Enrichment for T cells is performed by negative or positive selection with appropriate monoclonal antibodies coupled to columns or magnetic beads according to standard techniques. An aliquot of cells is analyzed for desired cell surface phenotype (e.g., CD4, CD8, CD3, CD14, etc.). Transduced cells are prepared for reinfusion according to established methods See, Abrahamsen et al., *J. Clin. Apheresis* 6:48–53, 1991; Carter et al. *J. Clin. Arpheresis* 4:113–117, 1988; Aebersold et al., *J. Immunol. Methods* 112: 1–7, 1988; Muul et al., *J. Immunol. Methods* 101: 171–181, 1987; and Carter et al., *Transfusion* 27:362–365, 1987).

In another embodiment, retroviral particles including a retroviral vector of the invention can be used to treat a heterologous graft which is then transplanted into the subject. For example, a retroviral vector of the invention can be used to infect a heart, which is subsequently transplanted into a subject requiring a heart transplant.

In Vivo Transformation of Cells

Retroviral particles containing a retroviral vector of the invention that reconstitute a heterologous nucleic acid sequence (e.g. a nucleic acid sequence encoding a therapeutic protein, a marker, or a toxin), can be administered directly to an organism for transduction of cells in vivo. In one embodiment, the heterologous nucleic acid sequence encodes a therapeutic protein for the treatment of a subject.

Administration is by any of the routes normally used for introducing a molecule into cells. The packaged nucleic acids are administered in any suitable manner, preferably with pharmaceutically acceptable carriers. Suitable methods of administering such packaged nucleic acids in the context of the present invention to a patient are available, and although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Injection solutions and suspensions can be prepared from sterile powders, granules, and tablets of the kind previously described. Cells transduced by the packaged nucleic acid as described above in the context of ex vivo therapy can also be administered intravenously or parenterally as described above. The dose administered to a subject, in the context of the present invention should be sufficient to effect a beneficial therapeutic response in the patient over time, or to inhibit infection by a pathogen. The dose will be determined by the efficacy of the particular heterologous nucleic acid sequence employed and the condition of the patient, as well as the body weight or surface area of the subject to be treated. The size of the dose also will be determined by the existence, nature, and extent of any adverse side-effects that accompany the administration of a particular vector, or transduced cell type in a particular patient.

In determining the effective amount of the retroviral vector to be administered in the treatment of a disease, the physician or other clinician evaluates symptom or clinical parameters, including the progression of the disease. In general, the dose equivalent of a naked nucleic acid from a vector is from about 1 µg to 100 µg for a typical 70 kilogram. The exact dosage of retroviral particles including a hybrid retroviral vector of the invention is dependent upon a variety of factors, including the age, weight, and sex of the subject to be treated, and the nature and extent of the disease or disorder to be treated. Effective doses can be extrapolated from dose-response curves derived from in vitro or animal model test systems.

Administration can be accomplished via single or divided doses. Methods of introduction include, but are not limited to, intradermal, intramuscular, intraperitoneal, intravenous, subcutaneous, intranasal, and oral routes. Administration can be by any convenient route, for example by infusion or bolus injection, by absorption through epithelial or mucocutaneous linings (e.g., oral mucosa, rectal and intestinal mucosa, etc.). In addition, the pharmaceutical compositions can be introduced into the central nervous system by any suitable route, including intraventricular and intrathecal injection; intraventricular injection can be facilitated by an intraventricular catheter, for example, attached to a reservoir, such as an Ommaya reservoir. Administration can be systemic or local. The retroviral particles of the invention can be administered together with other biologically active agents.

In one embodiment, it may be desirable to administer the pharmaceutical compositions of the invention locally to the area in need of treatment, for example, by local infusion during surgery, topical application, e.g., in conjunction with a wound dressing after surgery, by injection, through a catheter, by a suppository or an implant, such as a porous, non-porous, or gelatinous material, including membranes, such as silastic membranes, or fibers. In one embodiment, administration can be by direct injection at the site (or former site) of a malignant tumor or neoplastic or preneoplastic tissue.

The present invention also provides pharmaceutical compositions which include a therapeutically effective amount of the hybrid retroviral vectors, alone or with a pharmaceutically acceptable carrier.

Such carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate.

The pharmaceutical compositions or methods of treatment can be administered in combination with other therapeutic treatments, such as other antineoplastic or antitumorigenic therapies.

Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used in the present invention are normal saline and sesame oil.

Embodiments of the invention comprising medicaments can be prepared with conventional pharmaceutically acceptable carriers, adjuvants and counterions as would be known to those of skill in the art.

Example 10

Figure 9:
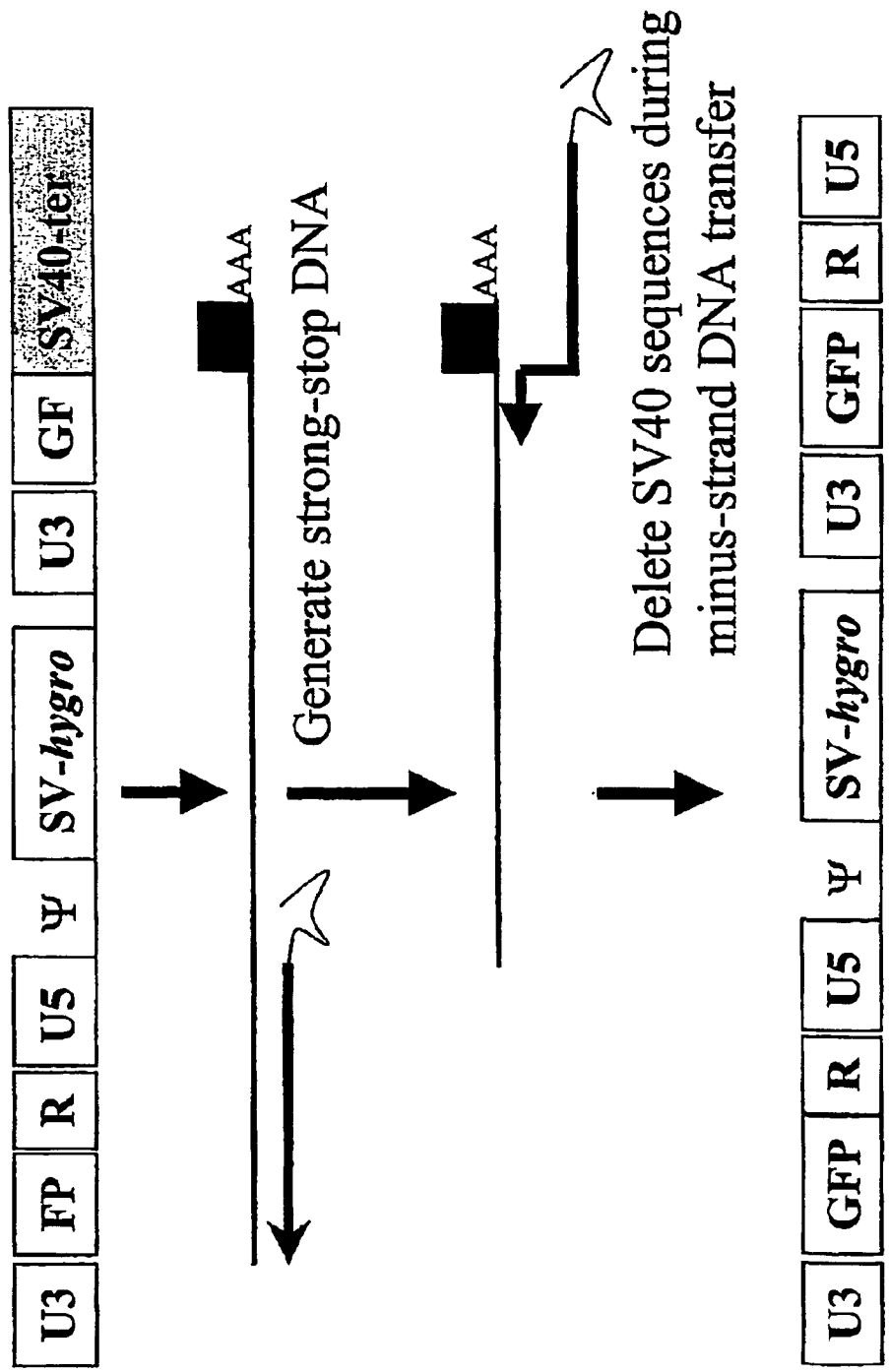
FIG. 9 is a schematic diagram of the integration of MS2, demonstrating the deletion of sequences 3' of the GF region.

Deletion of Sequences 3' of the 5' Portion of a Heterologous Nucleic Acid During Reconstitution In the plasmid pMS2, the R and U5 sequences of the 3' retroviral LTR were replaced by a DNA fragment containing a transcription termination signal from SV40. The DNA fragment inserted next to GF had 108 nucleotides inserted before the end of the AATAAA sequence (or AAUAAA in RNA), which is a transcription termination signal. In the cell, an endonuclease generally cleaves 11–30 nucleotides downstream from the AAUAAA signal. Therefore the structure of the viral RNA contains FP-R-U5 at the 5' end and U3-GF-SV40 sequences (119–138 nt) at the 3' end (see FIG. 9).

After infecting cells with virus containing MS2 RNA, approximately 92% of infected cell expresses GFP, indicating the F region was used to mediate strand transfer. In order for the transfer to occur from F region to F region, the sequences 3' to the GF region must be deleted during this process. In the case of MS2, GFP was reconstituted as the F region was used to mediate minus-strand DNA transfer, and the 119–138 nt sequences 3' to the GF were efficiently deleted during virus replication.

The deletion of the nucleotide sequence 3' to the GF was further confirmed by molecular characterization. Viral LTRs were PCR amplified from 9 cell clones containing MS2 proviruses expressing GFP. Direct DNA sequencing indicated that SV40 sequences were missing from the LTR, confirming the deletion of these sequences.

Figure 10:
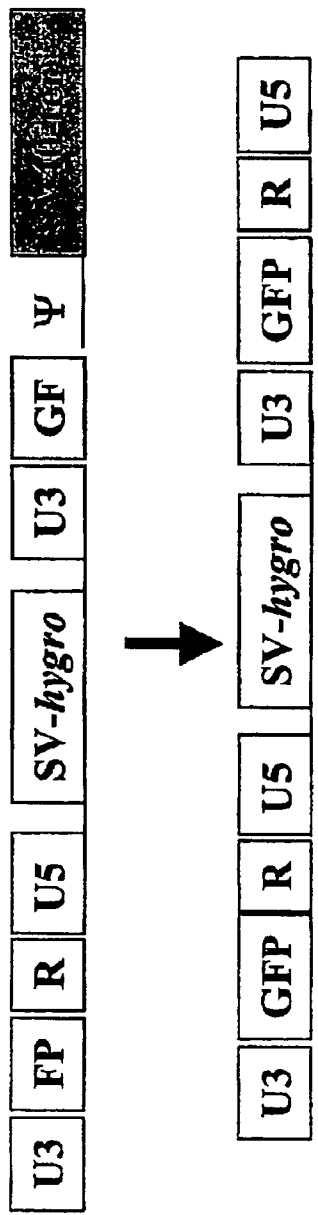
FIG. 10 is a schematic diagram of additional constructs with viral or non-viral sequences inserted 3' of the GF region. Integration of the virus in a cellular genome results in the deletion of the viral or non-viral sequences.
Figure 10:
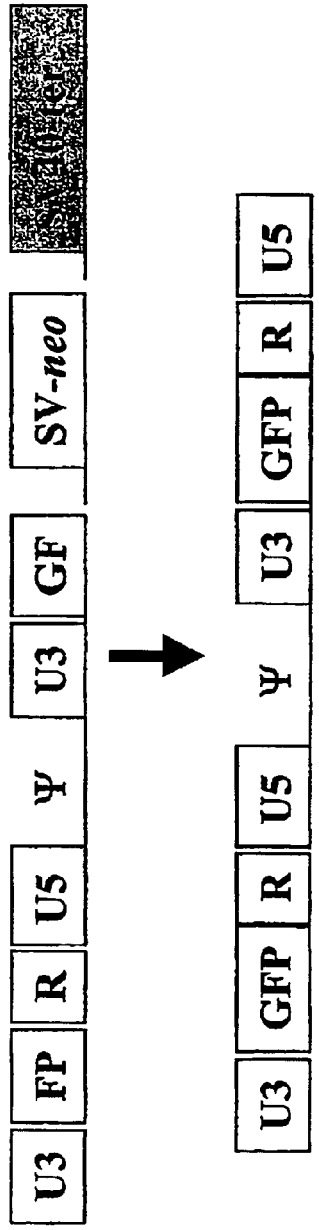

This example demonstrates that a sequence of interest can be inserted 3' to the 5' portion of the heterologous nucleic acid. The sequence of interest will be deleted during reconstitution of the heterologous gene. In this example, 119–138 nucleotide of SV40 sequences was deleted. In another embodiment, other viral sequences can be inserted 3' to the 5' portion of the heterologous nucleic acid. In a further embodiment, non-viral sequences can be inserted 3' of the 5' portion of the heterologous nucleic acid (see FIG. 10).

In one specific, non-limiting example, the sequence of interest is a viral sequence such as the packaging signal. Thus, the viral packaging signal is inserted 3' to the 5' heterologous nucleic acid. The viral RNA produced from this structure will contain the packaging signal. However, after reverse transcription, the heterologous nucleic acid will be used to mediate minus-strand DNA transfer and the packaging signal will be deleted.

In another specific, a selectable marker gene such as neomycin phosphotransferase gene (neo) is the sequence of interest. This sequence is inserted 3' to the 5' portion of heterologous nucleic acid in a viral vector. After transfection of the vector into a helper cell, the viral RNA is expressed, and thus the helper cell is resistant to neomycin or an analog of neomycin. This facilitates the selection of helper cells expressing the vector. However, after reverse transcription, the nucleic acid sequences encoding neo are deleted. Thus, cells infected with the vector are not neo resistant, as they do not contain the nucleic acid sequences encoding the drug-resistance gene.

Having illustrated and described the principles of generating a retroviral vector for use in the delivery of a nucleic acid sequence to a cell or subject, the art of the invention can be modified in arrangement and detail without departing from such principles. In view of the many possible embodiments to which the principles of my invention can be applied, it should be recognized that the illustrated embodiments are only examples of the invention and should not be taken as a limitation on the scope of the invention. Rather, the scope of the invention is in accord with the following claims. We therefore claim as my invention all that comes within the scope and spirit of these claims.

We claim:

1. A retroviral vector for gene reconstitution in vitro, comprising:
   a 3' portion of a heterologous nucleic acid sequence of a gene to be reconstituted;
   a 5' portion of the heterologous nucleic acid sequence of the gene to be reconstituted; and
   a viral nucleic acid comprising a R, U5 and U3 region, wherein (i) the combined 3' portion of the heterologous nucleic acid sequence and the 5' portion of the heterologous sequence have a size of less than seven kilobases, (ii) the 5' end of the 3' portion of the heterologous nucleic acid sequence comprises at least a 12 nucleotide direct repeat of the 3' end of the 5' portion of the heterologous nucleic acid sequence, (iii) the 3' portion of the heterologous nucleic acid sequence is linked to the viral nucleic acid at the 5' end, adjacent to the R and U5 regions, wherein the U5 region comprises a first att site (iv) the 5' portion of the heterologous nucleic acid sequence is linked to the 3' end of the viral nucleic acid at the 3' end, adjacent to the U3 region, wherein the U3 region comprises a second att site, and (v) transformation of a eukaryotic cell with the retroviral vector results in reconstitution and duplication of the heterologous nucleic acid sequence through primer template switching during reverse transcription and subsequent integration in the eukaryotic cell's genome.

2. The retroviral vector of claim 1, wherein the first att site is 5–15 bases in length.

3. The retroviral vector of claim 2, wherein the first att site is 7–13 bases in length.

4. The retroviral vector of claim 1, wherein the second att site is 5–15 bases in length.

5. The retroviral vector of claim 4, wherein the second att site is 7–13 bases in length.

6. The retroviral vector of claim 1, wherein the at least 12 nucleotide direct repeat of the 5' end of the 5' portion of the heterologous nucleic acid sequence comprises an about 20 to about 500 nucleotide direct repeat of the 3' end of the 5' portion of the heterologous nucleic acid sequence.

7. The retroviral vector of claim 1, wherein the heterologous nucleic acid sequence encodes a polypeptide.

8. The retroviral vector of claim 7, wherein the polypeptide is a selectable marker polypeptide, a therapeutic polypeptide, a toxic polypeptide, an antigen, or a cytokine.

9. The retroviral vector of claim 7, wherein the polypeptide is a selectable marker polypeptide selected from the group consisting of green fluorescent protein and β-galactosidase.

10. The retroviral vector of claim 7, wherein the polypeptide is an enzyme selected from the group consisting of neomycin phosphotransferase, hygromycin phosphotransferase, horseradish peroxidase and alkaline phosphatase.

11. The retroviral vector of claim 7, wherein the polypeptide is a toxic polypeptide selected from the group consisting of diphtheria toxin, herpesvirus thymidine kinase, pseudomonas exotoxin, cytosine deaminase, and ricin.

12. The retroviral vector of claim 7, wherein the polypeptide is an antigen.

13. The retroviral vector of claim 7, wherein the polypeptide is a cytokine selected from the group consisting of IL-2, IL-4, IL-6, IL-8, IL-12, TNF-α, TNF-β, and IFN-γ.

14. The retroviral vector of claim 1, wherein the heterologous nucleic acid sequence is an antisense nucleic acid or a ribozyme nucleic acid.

15. The retroviral vector of claim 1, wherein the 5' portion of the heterologous nucleic acid sequence is operably linked to a promoter.

16. The retroviral vector of claim 15, wherein the promoter is a retroviral promoter.

17. The retroviral vector of claim 15, wherein the promoter is a non-retroviral promoter.

18. The retroviral vector of claim 1, wherein the retroviral vector is deficient for the production of a viral gene product necessary for viral replication.

19. The retroviral vector of claim 18, wherein the retroviral vector is deficient for the, production of one or more of the gag, pol, or env gene products.

20. The retroviral vector of claim 1, wherein the retroviral vector is a Moloney Murine Leukemia Viral vector (MMLV), a spleen necrosis virus (SNV), spumaviral vector, avian leukosis vector, or a lentiviral vector.

21. The retroviral vector of claim 1, wherein the direct repeat at the 5' end of the 3' portion of the heterologous nucleic acid sequence is from about 12 to about 1500 bases in length.

22. The retroviral vector of claim 21, wherein the direct repeat at the 3' end of the 5' portion of the heterologous nucleic acid sequence is from about 12 to about 1000 bases in length.

23. A viral particle produced by transfecting a packaging cell line with the retroviral vector of claim 1.

24. An isolated eukaryotic host cell transformed with the retroviral vector of claim 1.

25. The isolated eukaryotic host cell of claim 24, wherein the cell is a human cell.

26. A method for transforming a cell, comprising:
contacting the cell in vitro with the retroviral vector of claim 1,
wherein the contact results in reconstitution and duplication of the heterologous nucleic acid sequence of the gene in the eukaryotic cell's genome.

27. The method of claim 26, wherein the gene encodes a marker polypeptide or a therapeutic polypeptide.

28. A kit comprising
a packaging means comprising the retroviral vector of claim 1.

29. A composition, comprising
(a) a retroviral vector for gene reconstitution,
a 3' portion of a heterologous nucleic acid sequence of a gene to be reconstituted;
a 5' portion of the heterologous nucleic acid sequence of the gene to be reconstituted; and
a viral nucleic acid comprising a R, U5 and U3 region,
wherein (i) the combined 3' portion of the heterologous nucleic acid sequence and the 5' portion of the heterologous sequence have a size of less than seven kilobases, (ii) the 5' end of the 3' portion of the heterologous nucleic acid sequence comprises at least a 12 nucleotide direct repeat of the 3' end of the 5' portion of the heterologous nucleic acid sequence, (iii) the 3' portion of the heterologous nucleic acid sequence is linked to the viral nucleic acid at the 5' end, adjacent to the R and U5 regions, wherein the U5 region comprises a first att site (iv) the 5' portion is linked to the 3' end of the viral nucleic acid at the 3' end, adjacent to the U3 region, wherein the U3 region comprises a second att site and (v) transformation of a eukaryotic cell in vitro with the retroviral vector results in reconstitution and duplication of the heterologous nucleic acid sequence through primer template switching during reverse transcription and subsequent integration in the eukaryotic cell's genome in vitro; and
(b) a carrier.

30. The retroviral vector of claim 1, further comprising a nucleic acid sequence of interest located 3' of the 5' portion of the heterologous nucleic acid sequence.

31. The retroviral vector of claim 30, wherein the nucleic acid sequence of interest is a packaging signal.

32. The retroviral vector of claim 30, wherein the nucleic acid sequence of interest encodes a selectable marker.

33. The retroviral vector of claim 32, wherein the selectable marker encodes neomycin resistance.

34. A method of deleting a nucleic acid sequence of interest from a retroviral vector, comprising:
transforming a cell with the retroviral vector of claim 30, wherein transformation of the cell with the retroviral vector results in integration of the retroviral vector into the cellular genome and deletion of the nucleic acid sequence of interest.

35. The method of claim 26, wherein the first att site is 5–15 bases in length.

36. The method of claim 35, wherein the first att site is 7–13 bases in length.

37. The method of claim 26, wherein the second att site is 5–15 bases in length.

38. The retroviral vector of claim 37, wherein the second att site is 7–13 bases in length.

39. The method of claim 26, wherein the at least 12 nucleotide direct repeat of the 5' end of the 3' portion of the heterologous nucleic acid sequence comprises an about 20 to about 500 nucleotide direct repeat of the 3' end of the 5' portion of the heterologous nucleic acid sequence.

40. The method of claim 26, wherein the 3' portion of the heterologous nucleic acid sequence is adjacent to the R region.

41. The method of claim 26, wherein the 5' portion of a heterologous nucleic acid sequence is adjacent to the U3 region.

42. The method of claim 26, wherein the 3' portion of a heterologous nucleic acid sequence is located from about 0 to about 1000 nucleotides from the R region.

43. The method of claim 26, wherein the 5' portion of a heterologous nucleic acid sequence is located from about 0 to about 1000 nucleotides from the U3 region.

44. The method of claim 26, wherein the heterologous nucleic acid sequence encodes a polypeptide.

45. The method of claim 1, wherein the combined 3' portion of the heterologous nucleic acid sequence and the 5' portion of the heterologous nucleic acid sequence have a size of less than one kilobase.

46. The composition of claim 29, wherein the combined 3' portion of the heterologous nucleic acid sequence and the 5' portion of the heterologous nucleic acid sequence have a size of less than one kilobase.

47. The retroviral vector of claim 1, further comprising a nucleotide sequence of interest 3' of the 5' U5 region and 5' of the of the U3 sequence.

48. The retroviral vector of claim 47, wherein the nucleotide sequence of interest comprises a packaging signal.

49. The retroviral vector of claim 47, wherein the nucleotide sequence of interest comprises a nucleic acid encoding drug resistance.

* * * * *

SEQUENCE LISTING

```
<160> NUMBER OF SEQ ID NOS: 11

<210> SEQ ID NO 1
<211> LENGTH: 35
<212> TYPE: DNA
<213> ORGANISM: Artificial Sequence
<220> FEATURE:
<223> OTHER INFORMATION: Oligonucleotide Primer

<400> SEQUENCE: 1
tctccgaatg gcgcgccgcc accatgagca agggc                              35

<210> SEQ ID NO 2
<211> LENGTH: 40
<212> TYPE: DNA
<213> ORGANISM: Artificial Sequence
<220> FEATURE:
<223> OTHER INFORMATION: Oligonucleotide Primer

<400> SEQUENCE: 2
cctatctcga ggcgcgcctc acttgtacag ctcgtccatg                         40
```

```
<210> SEQ ID NO 3
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 3
atcccgaatc ggcgccgcca ccatgagcaa gggc                          34

<210> SEQ ID NO 4
<211> LENGTH: 38
<212> TYPE: DNA
<213> ORGANISM: Artificial Sequence
<220> FEATURE:
<223> OTHER INFORMATION: Oligonucleotide Primer

<400> SEQUENCE: 4
gtcatgtcaa ggcgcctcac ttgtacagct cgtccatg                      38

<210> SEQ ID NO 5
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 5
atataggcct ggcgcgccat gcccgagggc tatg                          34

<210> SEQ ID NO 6
<211> LENGTH: 37
<212> TYPE: DNA
<213> ORGANISM: Artificial Sequence
<220> FEATURE:
<223> OTHER INFORMATION: Oligonucleotide Primer

<400> SEQUENCE: 6
cggtagcaat ggcgccaact tgacttcagc gcgggtc                       37

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 7
atgtttccag ggtgccccaa ggacc                                    25

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 8
tcaaacctcg acactagaca atcgg                                    25

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide Primer
```

-continued

```
<400> SEQUENCE: 9
cagcggagag ggtgaaggtg                                                    20

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 10
tcgtgggtag tcaatcactc agagg                                              25

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 11
cgacgcagtc tatcggaaga ct                                                 22
```